US011597696B2

(12) United States Patent
Miyazawa et al.

(10) Patent No.: US 11,597,696 B2
(45) Date of Patent: Mar. 7, 2023

(54) METHOD FOR PURIFYING POLYMERIZABLE FLUOROMONOMER BY DISTILLATION

(71) Applicant: Central Glass Company, Limited, Ube (JP)

(72) Inventors: Satoru Miyazawa, Kawagoe (JP); Yusuke Kuramoto, Kawasaki (JP); Asuka Sano, Kawagoe (JP); Ryo Nadano, Saitama (JP); Shinya Akiba, Fujimino (JP); Makoto Kobayashi, Tokyo (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 17/268,270

(22) PCT Filed: Sep. 25, 2018

(86) PCT No.: PCT/JP2018/035284
§ 371 (c)(1),
(2) Date: Feb. 12, 2021

(87) PCT Pub. No.: WO2020/035960
PCT Pub. Date: Feb. 20, 2020

(65) Prior Publication Data

US 2021/0317065 A1 Oct. 14, 2021

(30) Foreign Application Priority Data

Aug. 14, 2018 (JP) ............................. JP2018-152625

(51) Int. Cl.
*C07C 67/54* (2006.01)
*C07C 67/62* (2006.01)
*C08F 20/24* (2006.01)

(52) U.S. Cl.
CPC .............. *C07C 67/54* (2013.01); *C07C 67/62* (2013.01); *C08F 20/24* (2013.01)

(58) Field of Classification Search
CPC .......... C07C 67/54; C07C 67/62; C08F 20/24
See application file for complete search history.

(56) References Cited

U.S. PATENT DOCUMENTS

| | | | | |
|---|---|---|---|---|
| 7,029,556 | B1 | 4/2006 | Fauconet et al. | |
| 2003/0078352 | A1 | 4/2003 | Miyazawa et al. | |
| 2005/0165249 | A1 | 7/2005 | Komata et al. | |
| 2006/0217507 | A1* | 9/2006 | Miyazawa .............. | C08F 20/28 560/220 |
| 2010/0297564 | A1 | 11/2010 | Yamashita et al. | |
| 2015/0361026 | A1* | 12/2015 | Oomuro .................. | C07C 67/08 568/466 |
| 2019/0023641 | A1 | 1/2019 | Chretien et al. | |

FOREIGN PATENT DOCUMENTS

| | | | |
|---|---|---|---|
| CN | 102010334 | A | 4/2011 |
| EP | 1 749 812 | A1 | 2/2007 |
| JP | 7-316164 | A | 12/1995 |
| JP | 9-52861 | A | 2/1997 |
| JP | 2003-40840 | A | 2/2003 |
| JP | 2005-206587 | A | 8/2005 |
| JP | 4083399 | B2 | 4/2008 |
| JP | 4131005 | B2 | 8/2008 |
| JP | 4556491 | B2 | 10/2010 |
| JP | 4667035 | B2 | 4/2011 |
| JP | 4848112 | B2 | 12/2011 |
| JP | 4876312 | B2 | 2/2012 |
| JP | 5359052 | B2 | 12/2013 |
| JP | 2017-114812 | A | 6/2017 |
| WO | WO 2009/087889 | A1 | 7/2009 |
| WO | WO 2017/041204 | A1 | 3/2017 |

OTHER PUBLICATIONS

International Search Report (PCT/ISA/210) issued in PCT Application No. PCT/JP2018/035284 dated Oct. 23, 2018 with English translation (five (5) pages).

Japanese-language Written Opinion (PCT/ISA/237) issued in PCT Application No. PCT/JP2018/035284 dated Oct. 23, 2018 (three (3) pages).

Office Action in China Application No. 201880096448.4, dated Dec. 30, 2022, including English translation, 13 pages.

* cited by examiner

*Primary Examiner* — Yate' K Cutliff
(74) *Attorney, Agent, or Firm* — Crowell & Moring LLP

(57) ABSTRACT

The present invention is directed to a purification method for purifying a fluorine-containing polymerizable monomer of the formula (1), in which the fluorine-containing polymerizable monomer is purified by distillation in the coexistence of a phenolic compound A such as 6-tert-butyl-2,4-xylenol and a phenolic compound B such as 2,2'-methylene-bis(4-methyl-6-tert-butylphenol).

(1)

$$CH_2{=}C(R^1){-}C(=O){-}O{-}R^2{-}\left[C(CF_3)_2{-}OR^3\right]_m$$

By the combined use of the phenolic compound A and the phenolic compound B, it is possible to significantly suppress polymerization or oligomerization of the fluorine-containing polymerizable monomer even during industrial-production-scale distillation and efficiently purify the fluorine-containing polymerizable monomer by distillation.

8 Claims, No Drawings

METHOD FOR PURIFYING POLYMERIZABLE FLUOROMONOMER BY DISTILLATION

FIELD OF THE INVENTION

The present invention relates to a method for purifying by distillation a fluorine-containing polymerizable monomer, which is a raw material for fluorine-containing polymers usable as anti-reflective materials, photosensitive coating materials, resist materials for semiconductors, resist overlayer films, and the like. The present invention also relates to a method for producing a fluorine-containing polymer with the use of the fluorine-containing polymerizable monomer obtained by the distillation purification method such that the fluorine-containing polymer has a repeating unit derived from the fluorine-containing polymerizable monomer.

BACKGROUND ART

Because of fluorine's water repellency, oil repellency, low water absorption, heat resistance, weather resistance, corrosion resistance, transparency, photosensitivity, low refraction index, low dielectric property etc., fluorine compounds have been used and developed for a wide range of applications mainly in the field of advanced materials. For example, active researches and developments have been made on the applications of fluorine compounds for the formation of anti-reflective films with low refraction index and visible light transparency, optical devices with transparency in high wavelength band (optical communication wavelength band), resist materials with transparency in ultraviolet region, and the like.

Among others, a fluorine-containing polymerizable monomer of the formula (1) is a monomer compound that has a $(CF_3)_2(OR_3)C$ moiety derived from hexafluoroacetone and succeeds in incorporating polar groups in the same molecule in a well-balanced manner while attaining a high fluorine content (see Patent Document 1).

(1)

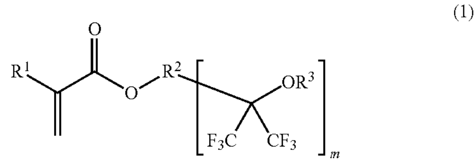

In the formula (1), $R^1$ is a group selected from a hydrogen atom, a halogen atom, a hydrocarbon group and a fluorine-containing alkyl group (wherein the fluorine-containing alkyl group is in straight or branched chain form and may contain a cyclic structure); $R^2$ is a divalent or trivalent organic group selected from an aliphatic hydrocarbon group (wherein the aliphatic hydrocarbon group is in straight or branched chain form and may contain a cyclic structure), an aromatic ring group and a composite group thereof, a part or all of hydrogen atoms of $R^2$ may be substituted with a fluorine atom or hydroxy group; $R^3$ is a hydrogen atom, a hydrocarbon group, a fluorine-containing alkyl group (wherein the fluorine-containing alkyl group is in straight or branched chain form and may contain a cyclic structure), or an aromatic ring group; the hydrocarbon group or fluorine-containing alkyl group as $R^3$ may have a divalent linking group selected from an ether group (—O—) and a carbonyl group (—(C═O)—); m is an integer of 1 to 2; and, when m is 2, two $R^3$ may be of the same kind or of different kinds.

It is known that: the above-mentioned fluorine-containing polymerizable monomer has excellent polymerizability; and a fluorine-containing polymer obtained by polymerization of the above-mentioned fluorine-containing polymerizable monomer combines transparency due to fluorine atoms with adhesion and processability due to polar groups, and exhibits good physical properties for use as anti-reflective film materials, optical device materials, resist materials, and the like (see Patent Document 1).

On the other hand, there has recently been a demand to improve the quality of optical materials and materials for semiconductors. Accordingly, there has also been a demand to improve the quality of polymerizable monomers used as raw materials for these materials. Various proposals have been made to provide polymerizable monomers with high purity, with less quality variations between production lots and at low cost.

As a technique of obtaining a single compound with a high purity from a mixture (crude product), there are known purification methods such as recrystallization, reprecipitation, distillation, sublimation, column chromatography etc. Column chromatography is an effective purification method at a laboratory level. In the case of mass production, however, this purification method is not efficient and becomes a cause of cost increase. Recrystallization, reprecipitation and sublimation are purification methods difficult to apply to compounds that are liquid in the vicinity of room temperature. In addition, each of these purification methods may require a complicated cleaning operation or a process step accompanied by a relatively large temperature change (e.g. a step of cooling from a temperature higher than 50° C. to a low temperature lower than or equal to 0° C.), and thus cannot be said as a convenient method.

By contrast, distillation is a superior purification method in that it is often convenient to purify a large amount of the target compound at one time in the case where the boiling point of the target compound is in the range of room temperature to several hundreds of degrees. For adoption of such a distillation purification method, however, some contrivance may be necessary to avoid decomposition or polymerization of the target compound during distillation.

It is well known to distill a easily polymerizable compound with the addition of a polymerization inhibitor. Many polymerization inhibitors, such as phenolic compounds (also called hydroquinone derivatives) and 2,2,6,6-tetramethylpiperidine 1-oxyl (TEMPO) derivatives, are provided as commercially available products. Examples of the use of these polymerization inhibitors are too numerous to enumerate. In the case of distilling a compound that claims high functionality, on the other hand, there is known a technique to use a polymerization inhibitor newly developed for the target compound rather than to use a commercially available polymerization inhibitor (see Patent Documents 2 and 3).

Further, there is disclosed an example of adding a contrivance to distillation equipment. For example, Patent Documents 4 and 5 each propose distillation equipment of special structure so as to suppress polymerization of the target compound inside the distillation equipment, prevent clogging of the distillation column due to polymer formation and obtain the target compound efficiently with reduced cleaning of the distillation equipment. This technique is certainly effective, but requires introduction of new distillation equipment.

Furthermore, there is generally widely known a technique to perform distillation while flowing oxygen gas in distillation equipment (which is so-called "aeration distillation") in order to enhance the effect of the phenolic polymerization inhibitor. There is also proposed the use of NOx such as nitrogen dioxide gas in combination with the polymerization inhibitor (see Patent Document 6) for the purpose of suppressing polymerization in the gas phase.

Under these circumstances, Patent Documents 7 and 8 disclose embodiments in which a 1,1-bis(trifluoromethyl)-1,3-diol acrylic acid ester compound of the formula (1a), which belongs to the compound of the above formula (1), is synthesized with the use of a compound selected from hydroquinone, methoquinone, 2,5-di-t-butylhydroquinone, 1,2,4-trihydroxybenzene, 2,5-bistetramethylbutylhydroquinone, leucoquinizarin, Nonflex F, Nonflex H, Nonflex DCD, Nonflex MBP, Ozonone 35, phenothiazine, tetraethylthiuram, disulfide, 1,1-diphenyl-2-picrylhydrazyl, 1,1-diphenyl-2-picrylhydrazine, Q-1300 (available from Wako Pure Chemical Industries, Ltd.) and Q-1301 (available from Wako Pure Chemical Industries, Ltd.) as a polymerization inhibitor.

(1a)

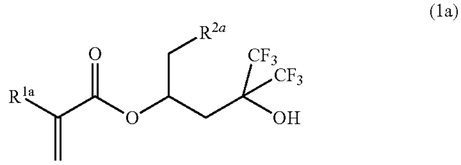

In the formula (1a), $R^{1a}$ is a hydrogen atom, a methyl group, an ethyl group, a n-propyl group, an isopropyl group, a n-butyl group, a sec-butyl group, a tert-butyl group, a fluoromethyl group, a difluoromethyl group, a trifluoromethyl group, or a perfluoroethyl group; and $R^{2a}$ is a hydrogen atom, a methyl group, an ethyl group, a n-propyl group, an isopropyl group, a n-butyl group, a sec-butyl group, a tert-butyl group, a fluoromethyl group, a difluoromethyl group, a trifluoromethyl group, or a perfluoroethyl group.

It is described in Patent Documents 7 and 8 that, after the step of synthesizing the compound, the resulting crude product is subjected to post-treatment such as water washing and then subjected to distillation purification. The polymerization inhibitor cannot be removed completely from the crude product of the formula (1a) just by performing several times of water washing. Thus, a part of the polymerization inhibitor added in the synthesis step is used as it is as a polymerization inhibitor during the distillation in the embodiments of these patent documents. In Example 2 of Patent Document 7, however, the polymerization inhibitor (phenothiazine) used in the synthesis step remains in the system; and the distillation takes place by separately adding some amount of the polymerization inhibitor (phenothiazine) into the system immediately before the initiation of the distillation.

PRIOR ART DOCUMENTS

Patent Documents

Patent Document 1: Japanese Patent No. 4083399
Patent Document 2: Japanese Patent No. 4876312
Patent Document 3: Japanese Patent No. 4556491
Patent Document 4: Japanese Laid-Open Patent Publication No. 2017-114812
Patent Document 5: Japanese Patent No. 4848112
Patent Document 6: Japanese Patent No. 4131005
Patent Document 7: Japanese Patent No. 4667035
Patent Document 8: Japanese Patent No. 5359052

SUMMARY OF THE INVENTION

Problems to be Solved by the Invention

A fluorine-containing polymerizable monomer as a target compound of the present invention is of the following general formula (1).

(1)

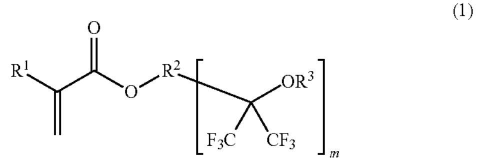

In the formula (1), the definitions of respective symbols are the same as above.

As a distillation purification technique for the monomer compound of the formula (1), Patent Documents 7 and 8 disclose a method of distilling the monomer compound in the presence of a polymerization initiator selected from phenolic compounds (hydroquinone derivatives) such as hydroquinone, methoquinone and 1,2,4-trihydroxybenzene and nitrogen-containing polymerization inhibitors such as phenothiazine, 1,1-diphenyl-2-picrylhydrazyl and Nonflex F (N,N'-di-2-naphthyl-para-phenylenediamine) as mentioned above. The presence of such a polymerization inhibitor makes it possible to significantly suppress polymerization of the monomer compound under heating during the distillation, as compared to the case of performing distillation in the absence of a polymerization inhibitor. This leads to a tendency of increase in distillation yield and makes it less likely that solid deposition will occur in distillation equipment.

Among polymerization inhibitors, "phenolic compounds (hydroquinone derivatives)" are superior polymerization inhibitors that are low in price and each exhibit a high polymerization inhibiting effect by addition of a small amount thereof. In addition, "phenolic compounds" are advantageous over nitrogen-containing polymerization inhibitors in that, when the compound of the formula (1) is distilled with the use of a phenolic compound as a polymerization inhibitor, the occurrence of a coloring phenomenon (such as yellow discoloration) during distillation can be suppressed to a low level.

It has however been found that the following problem arises in the case of using a "phenolic compound" as a polymerization inhibitor during distillation of the compound of the formula (1).

When the compound of the formula (1) is purified by distillation, local polymerization of the compound is likely to occur during the distillation as the amount of the compound charged in the distillation vessel becomes relatively large. More specifically, the target compound (main fraction) is smoothly obtained with a high purity by distillation in the presence of any of the above-mentioned phenolic compounds in the case of performing the distillation at a laboratory level where the amount of the compound of the formula (1) charged in the distillation vessel is 500 g or less (typically 100 g or less). In the laboratory-level distillation, it is often the case that there is found no particular problem in distillation operation. In the case of performing the distillation at a level where the amount of the compound of the formula (1) charged in the distillation vessel exceeds the above value (that is, exceeds 500 g) (hereinafter occasionally referred to as "mass-scale distillation" in the present specification), however, it becomes likely that local polymerization or oligomerization of the compound will occur. This tends to result in a phenomenon of local solid deposition inside the distillation equipment (i.e. in any of the bottom (still), the distillation column and the distillate). Since such a local solid deposition phenomenon is not always confirmed in the laboratory-level distillation, it is assumed that an increase in the heating time due to scale-up of the distillation process and a decrease in the heat removal efficiency of the distillation equipment are the cause of local solid deposition.

Once even a small amount of solid deposit is formed in the distillation equipment, the distillation column may be clogged. In the occurrence of clogging of the distillation column, it becomes necessary to disassemble and clean the distillation equipment. Further, the operation of discharging a bottom liquid from the distillation column may become complicated when a solid deposit is formed in the distillation equipment. Consequently, there arises a deterioration of productivity (production yield).

In view of the foregoing, the present inventors have made attempts to variously change the kind of the "phenolic compound" as the polymerization initiator in the process of purifying the fluorine-containing polymerizable monomer (i.e. the compound of the formula (1)) by "mass-scale distillation".

Although the use of various kinds of phenolic compounds have been attempted, either one of these attempts does not easily provide an improvement to the tendency of solid deposit formation in any of the bottom (still), the distillation column and the distillate during the "mass-scale distillation". In accordance with the tendency of solid deposit formation, there is observed a tendency that a high-molecular-weight component (i.e. a chemical species having a peak in polymer/oligomer region is easily detected (see the after-mentioned Comparative Examples).

Based on the above background, there has been a demand for a novel distillation purification method capable of purifying the fluorine-containing polymerizable monomer of the formula (1) by "mass-scale distillation" with the use of a "phenolic compound" as a good polymerization inhibitor while suppressing polymerization of the fluorine-containing monomer.

Means for Solving the Problems

The present inventors have made intensive studies to solve the above-mentioned problem and resultantly found that, when the fluorine-containing polymerizable monomer of the formula (1) is subjected to distillation with the combined use of a "phenolic compound A" of the following formula (2) and a "phenolic compound B" of the following formula (3) as polymerization inhibitors, it is possible to suppress polymerization or oligomerization of the fluorine-containing monomer and more smoothly perform distillation purification of the fluorine-containing monomer even on a mass scale (e.g. on a scale where the charge amount of the fluorine-containing monomer compound of the formula (1) exceeds 500 g).

[Phenolic Compound A]

(2)

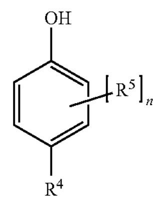

In the formula (2), $R^4$ and $R^5$ are each independently a hydrogen atom, a hydroxy group, an alkoxy group of 1 to 4 carbon atoms (wherein the alkoxy group can be in straight or branched chain form), an alkyl group of 1 to 4 carbon atoms (wherein the alkyl group can be in straight or branched chain form), an alkyl group having a cyclic structure, or an unsubstituted aromatic ring group; $R^4$ and $R^5$ may be of the same kind or of different kinds; n is an integer of 1 to 2; and, when n is 2, a plurality of $R^5$ may be of the same kind or of different kinds.

[Phenolic Compound B]

(3)

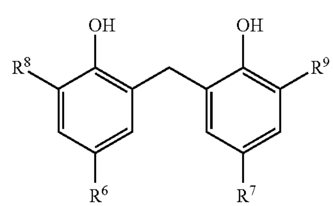

In the formula (3), $R^6$, $R^7$, $R^8$ and $R^9$ are each independently a hydrogen atom, a hydroxy group, an alkoxy group of 1 to 4 carbon atoms (wherein the alkoxy group can be in straight or branched chain form), an alkyl group of 1 to 4 carbon atoms (wherein the alkyl group can be in straight or branched chain form), an alkyl group having a cyclic structure, or an aromatic ring group; and $R^6$, $R^7$, $R^8$ and $R^9$ may be of the same kind or of different kinds.

In the case of distilling the monomer compound of the formula (1) on a mass scale with the use of only the "phenolic compound A" as a polymerization inhibitor or with the use of only the "phenolic compound B" as a polymerization inhibitor, polymerization or oligomerization of the monomer compound in the distillation equipment (e.g. bottom or distillation column) tends to be observed. In the case of distilling the monomer compound of the formula (1) with the combined use of the "phenolic compound A" and the "phenolic compound B", by contrast, polymerization or oligomerization of the monomer compound is sufficiently suppressed even when the total amount of the polymerization inhibitors is the same as that in the above case. The reason for this is not certain, but is assumed to be that there occurs a pecial synergistic effect exceeding the simple sum of the polymerization inhibiting effects of the "phenolic compound A" and the "phenolic compound B" in the distillation system.

Heretofore, there has not been proposed the idea of purifying the fluorine-containing polymerizable monomer of the formula (1) by distillation with the use of two specific phenolic compounds as polymerization inhibitors.

The present inventors have further found that, when the fluorine-containing polymerizable monomer of the formula (1) obtained as a high-purity fraction by distillation with the use of the "phenolic compound A" and the "phenolic compound B" in combination as a plurality of polymerization inhibitors is subsequently subjected to polymerization conditions, the desired polymerization reaction proceeds without hindrance whereby it is possible to form a fluorine-containing polymer (homopolymer or heteropolymer) with a repeating unit of the following formula (4). The present invention is established based on these findings.

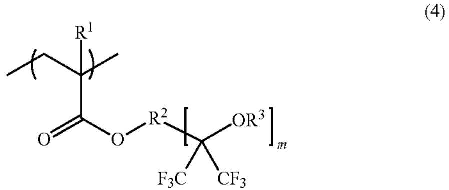

In the formula (4), the definitions of $R^1$, $R^2$, $R^3$ and m are the same as in the formula (1).

In other words, the present invention provides an excellent method of purifying a fluorine-containing polymerizable monomer of the formula (1) by distillation. The present invention also provides a method of producing a fluorine-containing polymer with a repeating unit of the formula (4) by obtaining the fluorine-containing polymerizable monomer with a high purity by the aforementioned distillation purification method and polymerizing the obtained fluorine-containing polymerizable monomer.

More specifically, the present invention includes the following aspects.

[Aspect 1]

A purification method for purifying a fluorine-containing polymerizable monomer of the following general formula (1), comprising the following first step:

First Step: a distillation purification step of distilling the fluorine-containing polymerizable monomer in the coexistence of a phenolic compound A of the following formula (2) and a phenolic compound B of the following formula (3), thereby obtaining the fluorine-containing polymerizable monomer as a distillation fraction

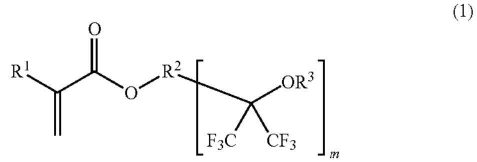

where $R^1$ is a group selected from a hydrogen atom, a halogen atom, a hydrocarbon group and a fluorine-containing alkyl group (wherein the fluorine-containing alkyl group is in straight or branched chain form and may contain a cyclic structure); $R^2$ is a divalent or trivalent organic group selected from an aliphatic hydrocarbon group (wherein the aliphatic hydrocarbon group is in straight or branched chain form and may contain a cyclic structure), an aromatic ring group and a composite group thereof, a part or all of hydrogen atoms of $R^2$ may be substituted with a fluorine atom or hydroxy group; $R^3$ is a hydrogen atom, a hydrocarbon group, a fluorine-containing alkyl group (wherein the fluorine-containing alkyl group is in straight or branched chain form and may contain a cyclic structure), or an aromatic ring group; the hydrocarbon group or fluorine-containing alkyl group as $R^3$ may have a divalent linking group selected from an ether group (—O—) and a carbonyl group (—(C═O)—); m is an integer of 1 to 2; and, when m is 2, two $R^3$ may be of the same kind or of different kinds,

[Phenolic Compound A]

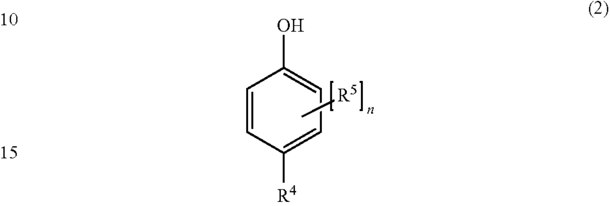

where $R^4$ and $R^5$ are each independently a hydrogen atom, a hydroxy group, an alkoxy group of 1 to 4 carbon atoms (wherein the alkoxy group can be in straight or branched chain form), an alkyl group of 1 to 4 carbon atoms (wherein the alkyl group can be in straight or branched chain form), an alkyl group having a cyclic structure, or an unsubstituted aromatic ring group; $R^4$ and $R^5$ may be of the same kind or of different kinds; n is an integer of 1 to 2; and, when n is 2, a plurality of $R^5$ may be of the same kind or of different kinds,

[Phenolic Compound B]

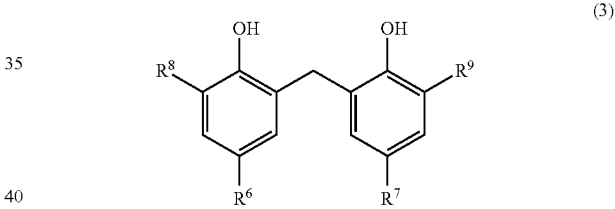

where $R^6$, $R^7$, $R^8$ and $R^9$ are each independently a hydrogen atom, a hydroxy group, an alkoxy group of 1 to 4 carbon atoms (wherein the alkoxy group can be in straight or branched chain form), an alkyl group of 1 to 4 carbon atoms (wherein the alkyl group can be in straight or branched chain form), an alkyl group having a cyclic structure, or an aromatic ring group; and $R^6$, $R^7$, $R^8$ and $R^9$ may be of the same kind or of different kinds.

[Aspect 2]

The purification method according to Aspect 1, wherein $R^4$ and $R^5$ in the phenolic compound A are each independently selected from the group consisting of a hydrogen atom, a methyl group, a methoxy group, an ethyl group, an ethoxy group, a n-propyl group, a n-propyloxy group, an i-propyl group, an i-propyloxy group, a n-butyl group, a n-butyloxy group, an i-butyl group, an i-butyloxy group, a t-butyl group, a t-butyloxy group and a hydroxy group with the proviso that at least one of $R^4$ and $R^5$ is not a hydrogen atom, and wherein $R^6$, $R^7$, $R^8$ and $R^9$ in the phenolic compound B are each independently selected from the group consisting of a hydrogen atom, a methyl group, a methoxy group, an ethyl group, an ethoxy group, a n-propyl group, a n-propyloxy group, an i-propyl group, an i-propyloxy group, a n-butyl group, a n-butyloxy group, an i-butyl group, an i-butyloxy group, a t-butyl group, a t-butyloxy group and a hydroxy group with the proviso that at least one of $R^6$, $R^7$, $R^8$ and $R^9$ is not a hydrogen atom.

[Aspect 3]

The purification method according to Aspect 1, wherein the phenolic compound A is at least one selected from the group consisting of 6-tert-butyl-2,4-xylenol and methoquinone, and wherein the phenolic compound B is at least one selected from the group consisting of 2,2'-methylene-bis(4-methyl-6-tert-butylphenol) and 2,2'-methylene-bis(4-ethyl-6-tert-butylphenol).

[Aspect 4]

The purification method according to Aspect 1, wherein the phenolic compound A is 6-tert-butyl-2,4-xylenol, and wherein the phenolic compound B is 2,2'-methylene-bis (4-methyl-6-tert-butylphenol).

[Aspect 5]

The purification method according to any one of Aspects 1 to 4, wherein a mass ratio of the phenolic compound A and the phenolic compound B is in a range of 1:0.1 to 1:10.

[Aspect 6]

The purification method according to any one of Aspects 1 to 5, wherein the fluorine-containing polymerizable monomer of the formula (1) is a fluorine-containing polymerizable monomer of the following formula (1a), (1b) or (1c)

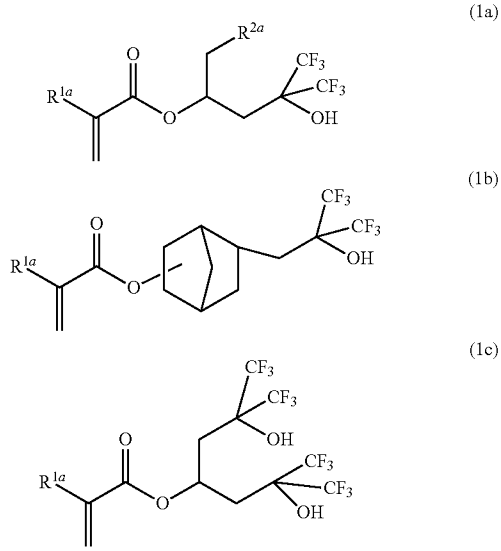

where $R^{1a}$ is a hydrogen atom, a methyl group, an ethyl group, a n-propyl group, an isopropyl group, a n-butyl group, a sec-butyl group, a tert-butyl group, a fluoromethyl group, a difluoromethyl group, a trifluoromethyl group, or a perfluoroethyl group; and $R^{2a}$ is a hydrogen atom, a methyl group, an ethyl group, a n-propyl group, an isopropyl group, a n-butyl group, a sec-butyl group, a tert-butyl group, a fluoromethyl group, a difluoromethyl group, a trifluoromethyl group, or a perfluorethyl group.

[Aspect 7]

The purification method according to any one of Aspects 1 to 6, wherein the fluorine-containing polymerizable monomer of the formula (1) is a product of condensation between a compound of the following formula (5) and a compound of the following formula (6), and wherein the condensation is performed in the presence of at least one of the phenolic compound A and the phenolic compound B

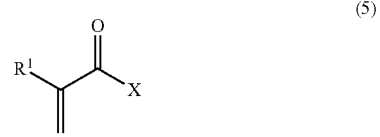

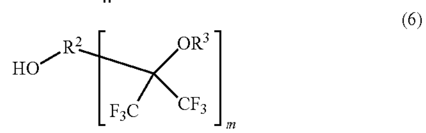

where X is a hydroxy group, a halogen atom, an alkoxy group, or an oxocarbonyl group; and the definitions of other symbols are the same as in the formula (1).

[Aspect 8]

A method of producing a fluorine-containing polymer with a repeating unit of the following general formula (4), comprising, after a first step of obtaining a fluorine-containing polymerizable monomer by the purification method according to any one of Aspects 1 to 7, a second step of polymerizing the fluorine-containing polymerizable monomer obtained by the first step, thereby forming the fluorine-containing polymer with the repeating unit of the general formula (4)

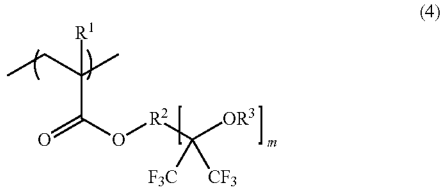

wherein the definitions of $R^1$, $R^2$, $R^3$ and m are the same as in Aspect 1.

Effects of the Invention

The adoption of the purification method according to the present invention provides the effect of distilling the fluorine-containing polymerizable monomer of the formula (1) on a mass scale (particularly on a scale where the charge amount of the fluorine-containing polymerizable monomer exceeds 500 g) while significantly suppressing polymer forming reaction (polymerization or oligomerization) of the fluorine-containing polymerizable monomer.

When the purification method is implemented as the first step, the fluorine-containing polymerizable monomer is obtained with a high purity as a distillation fraction in the first step. The obtained fluorine-containing polymerizable monomer is subsequently subjected to polymerization conditions and thereby smoothly converted to a fluorine-containing polymer with the repeating unit of the formula (4). Thus, the combination of the first step (distillation purification step) and the second step (polymerization step) provides the effect of producing the fluorine-containing polymer more advantageously than conventional methods.

DETAILED DESCRIPTION OF EMBODIMENTS

Hereinafter, the present invention will be described in detail below. It should be understood that: the scope of the present invention is not limited to the following embodiments; and various changes and modifications of the following embodiments can be made as appropriate within the range that does not depart from the scope of the present invention. All of the publications cited in the present specification, such as prior art documents, unexamined patent publications, patent publications and other patent documents, are herein incorporated by reference.

[Fluorine-containing Polymerizable Monomer]

A fluorine-containing polymerizable monomer as the target compound of the present invention is of the following formula (1).

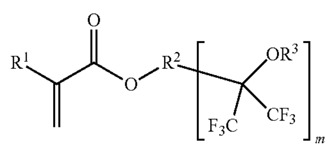

(1)

In the formula (1), the definitions of respective symbols are the same as above.

The fluorine-containing polymerizable monomer has a structure in which a (meth)acrylic moiety and a hexafluoroacetone-derived moiety coexist in one molecule. This monomer compound shows an adequate polarity while being provided with a plurality of fluorine atoms, and also shows good polymerizability.

In the formula (1), $R^1$ is a group selected from the group consisting of a hydrogen atom, a halogen atom, a hydrocarbon group and a fluoroalkyl group (wherein the fluoroalkyl group is in straight or branched chain form and may contain a cyclic structure). As the halogen atom, fluorine is preferred. Examples of the hydrocarbon group include alkyl groups of 1 to 10 carbon atoms (each of which can have a straight or branched chain structure or a cyclic structure), phenyl and tolyl. As the hydrocarbon group, preferred is methyl. Examples of the fluoroalkyl group include those of 1 to 6 carbon atoms. As the fluoroalkyl group, preferred is trifluoromethyl. Among others, hydrogen and methyl are particularly preferred as $R^1$ because, in such a case, an acrylic acid derivative or methacrylic acid derivative which is easily available on a mass scale is used as the raw material for synthesis of the fluorine-containing polymerizable monomer as will be explained later.

In the formula (1), $R^2$ is a divalent organic group (in the case of m=1) or a trivalent organic group (in the case of m=2). The divalent or trivalent organic group is a group selected from an aliphatic hydrocarbon group (wherein the aliphatic hydrocarbon group is in straight or branched chain form and may contain a cyclic structure), an aromatic ring group and a composite group thereof. Apart or all of hydrogen atoms of the organic group R2 may be substituted with a fluorine atom or hydroxy group. Examples of the aliphatic hydrocarbon group include those of 1 to 20 carbon atoms. Examples of the aromatic ring group include those each having two or three bonds to the benzene ring. Example of the composite group include those each having an aliphatic hydrocarbon unit and an aromatic ring unit in a serial or parallel relationship as one $R^2$ group.

Among others, the following functional groups (where each dotted line represents a bond) are preferred as $R^2$ because the monomer having any of these functional groups is usable as a raw material for formation of a polymer with good physical properties.

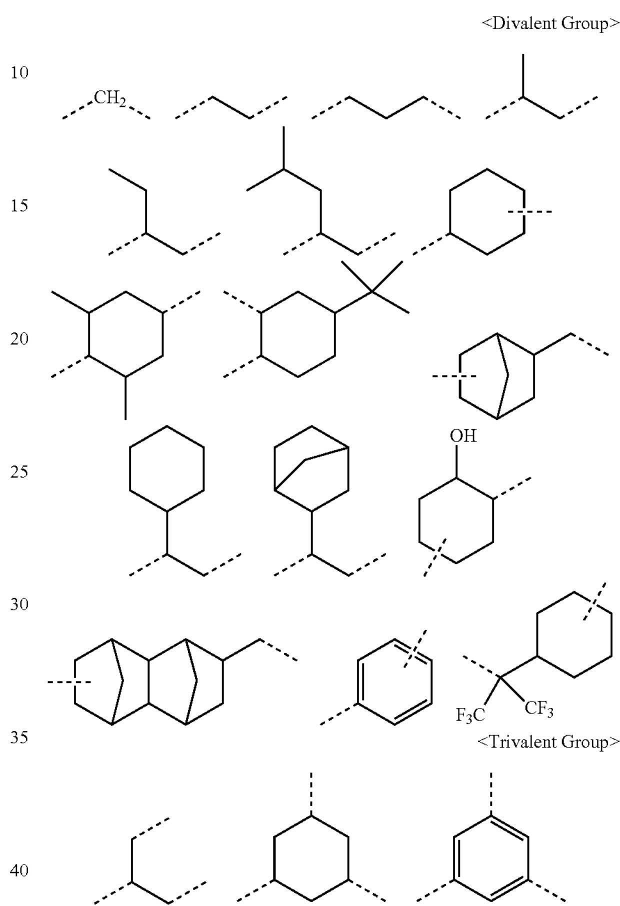

Further, $R^3$ is a hydrogen atom, a hydrocarbon group, a fluoroalkyl group (wherein the fluoroalkyl group is in straight or branched chain form and may contain a cyclic structure), or an aromatic ring group. The hydrocarbon group or fluoroalkyl group may have a divalent linking group selected from an ether group (—O—) and a carbonyl group (—(C═O)—) in its structure. Examples of the hydrocarbon group include those of 1 to 20 carbon atoms. As the hydrocarbon group, an alkyl group of 1 to 6 carbon atoms is preferred. Examples of the fluoroalkyl group include those of 1 to 6 carbon atoms. As the fluoroalkyl group, a $CF_3$ group is preferred. Examples of the aromatic ring group include phenyl and tolyl. Herein, the hydrocarbon group or fluoroalkyl group having a divalent linking group selected from an ether group (—O—), a carbonyl group (—(C═O)—) etc. in its structure means that a —O— bond, —(C═O)— bond, —(C═O)O— bond etc. is inserted between carbon atoms of the hydrocarbon group or fluoroalkyl group.

Among various examples of the fluorine-containing polymerizable monomer of the formula (1), preferred are those of the following formulas (1a), (1b) and (1c) because polymer resins obtained from these monomers shows excellent performance.

(1a)

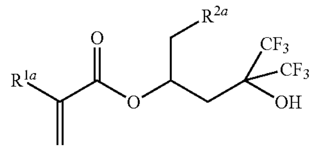

(1b)

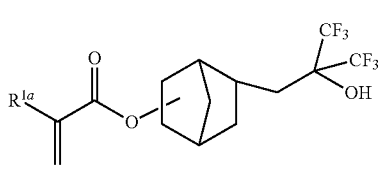

(1c)

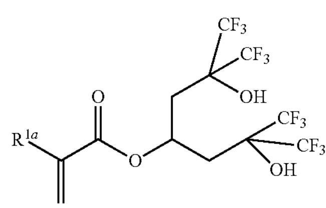

In the formulas (1a), (1b) and (1c), the definitions of respective symbols are the same as above.

As $R^{1a}$ in the formulas (1a), (1b) and (1c), hydrogen and methyl are particularly preferred. As $R^{2a}$ in the formulas (1a), (1b) and (1c), hydrogen, methyl, ethyl, n-propyl, i-propyl and trifluoromethyl are preferred. Particularly preferred as $R^{2a}$ is hydrogen.

[Polymerization Inhibitors]

In the present invention, the distillation purification step (first step) is conducted using phenolic compounds A and B of the following formulas as polymerization inhibitors.

[Phenolic Compound A]

(2)

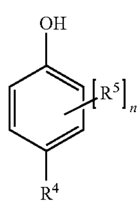

In the formula (2), $R^4$ and $R^5$ are each independently a hydrogen atom, a hydroxy group, an alkoxy group of 1 to 4 carbon atoms (wherein the alkoxy group can be in straight or branched chain form), an alkyl group of 1 to 4 carbon atoms (wherein the alkyl group can be in straight or branched chain form), an alkyl group having a cyclic structure, or an unsubstituted aromatic ring group; $R^4$ and $R^5$ may be of the same kind or of different kinds; n is an integer of 1 to 2; and, when n is 2, a plurality of $R^5$ may be of the same kind or of different kinds.

[Phenolic Compound B]

(3)

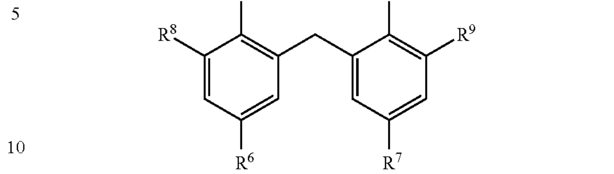

In the formula (3), $R^6$, $R^7$, $R^8$ and $R^9$ are each independently a hydrogen atom, a hydroxy group, an alkoxy group of 1 to 4 carbon atoms (wherein the alkoxy group can be in straight or branched chain form), an alkyl group of 1 to 4 carbon atoms (wherein the alkyl group can be in straight or branched chain form), an alkyl group having a cyclic structure, or an aromatic ring group; and $R^6$, $R^7$, $R^8$ and $R^9$ may be of the same kind or of different kinds Preferable examples of the phenolic compound A include those in which $R^4$ and $R^5$ are each independently selected from the group consisting of hydrogen, methyl, methoxy, ethyl, ethoxy, n-propyl, n-propyloxy, i-propyl, i-propyloxy, n-butyl, n-butyloxy, i-butyl, i-butyloxy, t-butyl, t-butyloxy and hydroxy with the proviso that at least one of $R^4$ and $R^5$ is not hydrogen. In the case where both of $R^4$ and $R^5$ are hydrogen, the phenolic compound A is an unsubstituted phenol. Although the unsubstituted phenol has the function of a polymerization inhibitor, the phenolic compound other than the unsubstituted phenol is more preferred as the phenolic compound A in the present invention.

Preferable example of the phenolic compound B are those in which $R^6$, $R^7$, $R^8$ and $R^9$ are each independently selected from the group consisting of hydrogen, methyl, methoxy, ethyl, ethoxy, n-propyl, n-propyloxy, i-propyl, i-propyloxy, n-butyl, n-butyloxy, i-butyl, i-butyloxy, t-butyl, t-butyloxy and hydroxy with the proviso that at least one of $R^6$, $R^7$, $R^8$ and $R^9$ is not hydrogen. Although the phenolic compound in which all of $R^6$, $R^7$, $R^8$ and $R^9$ are hydrogen has the function of a polymerization inhibitor, the phenolic compound in which at least one of $R^6$, $R^7$, $R^8$ and $R^9$ is not hydrogen is more preferred as the phenolic compound B in the present invention.

It is a preferable embodiment of the present invention to use the above-mentioned "preferable" phenolic compounds A and B in combination as the polymerization inhibitors.

The following are more preferable examples of the phenolic compound A and more preferable examples of the phenolic compound B. It is a more preferable embodiment of the present invention to use these phenolic compounds A and B in combination.

More Preferable Examples of Phenolic Compound A

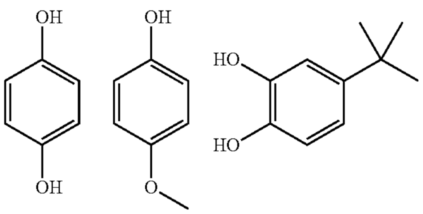

-continued
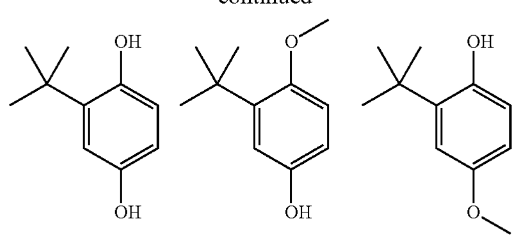
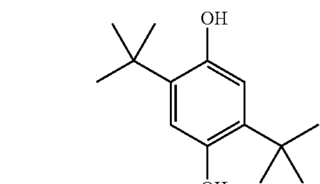
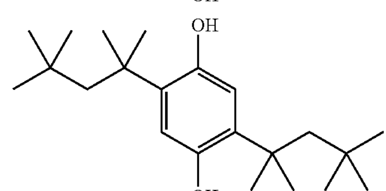
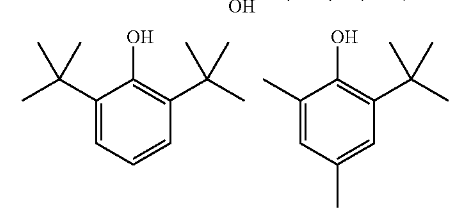
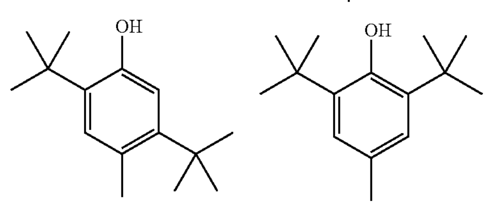
More Preferable Examples of Phenolic Compound B
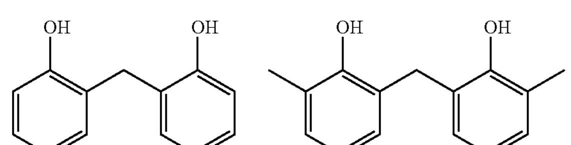
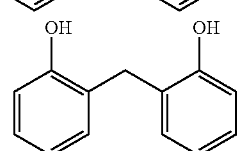
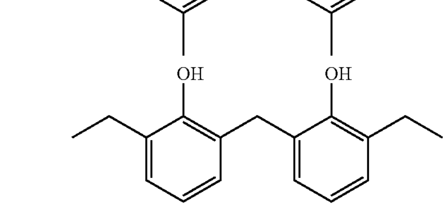
-continued
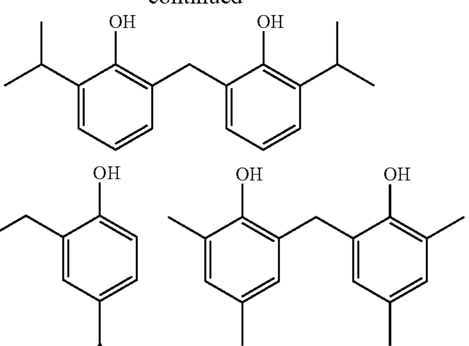
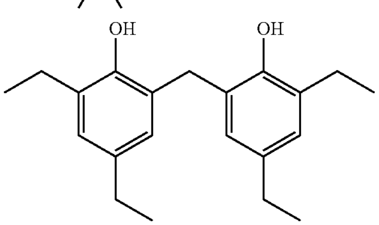
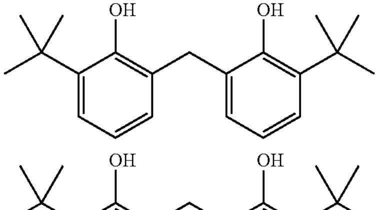
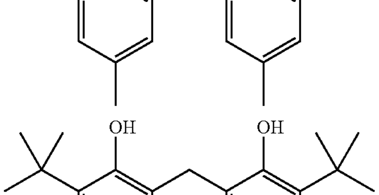
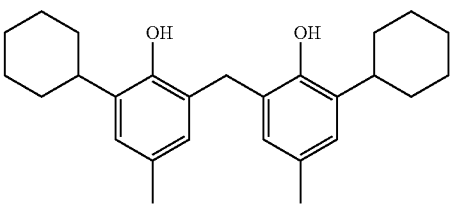

-continued

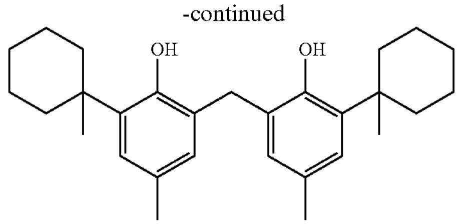

Among others, it is particularly preferable that: the phenolic compound A is at least one selected from the group consisting of 6-tert-butyl-2,4-xylenol and methoquinone; and the phenolic compound B is at least one selected from the group consisting of 2,2'-methylene-bis(4-methyl-6-tert-butylphenol) and 2,2'-methylene-bis(4-ethyl-6-tert-butylphenol).

It is more particularly preferable that: the phenolic compound A is 6-tert-butyl-2,4-xylenol; and the phenolic compound B is 2,2'-methylene-bis(4-methyl-6-tert-butylphenol).

It is not excluded that a plurality of kinds of phenolic compounds A or a plurality of kinds of phenolic compounds B are used. However, the use of so many kinds of phenolic compounds results in complicated quality management. In general, the combined use of one kind of phenolic compound A and one kind of phenolic compound B is particularly preferred.

There is no particular limitation on the mass ratio of the phenolic compound A and the phenolic compound B. The mass ratio of the phenolic compound A and the phenolic compound B is preferably in the range of 1:0.1 to 1:10 because, in such a mass ratio range, the effect of the combined use of these phenolic compounds is enhanced. The mass ratio of the phenolic compound A and the phenolic compound B is more preferably in the range of 1:0.2 to 1:5. Typically, it is particularly preferable that the mass ratio of the phenolic compound A and the phenolic compound B is in the range of 1:0.2 to 1:2.

Herein, the basis for calculating the "mass ratio" of the phenolic compound A and the phenolic compound B is the "total mass of the phenolic compounds dissolving in the fluorine-containing polymerizable monomer of the formula (1) charged in the distillation vessel during the distillation purification step (first step)". In the case where any of the above-mentioned phenolic compounds is added as a polymerization inhibitor in the synthesis step of the fluorine-containing polymerizable monomer in advance of the distillation purification step and a part of the added phenolic compound remains in the system, the mass of the phenolic compound A or B used for the calculation of the "quantity ratio" is the sum of the "mass of the phenolic compound present from before the distillation step and remaining in the system" and the "mass of the phenolic compound added at the initiation of the distillation step". The specific adjustment method of the mass ratio will be explained later in the later section "First Step (Distillation Purification Step".

The respective steps relevant to the present invention are shown in the following scheme 1.

Scheme 1

[Synthesis Step of Fluorine-containing Polymerizable Monomer (General Formula (1))] also referred to as Synthesis Step

↓

[Post-Treatment Step]

↓

[Distillation Purification Step (First Step)]

↓

[Polymerization Step (Second Step)]

In the present invention, the "distillation purification step (first step)" is the most noticeable step. It is however preferable that a polymerization inhibitor coexists in the system during the "synthesis step" prior to the distillation purification step. Typically, a part of the polymerization inhibitor used in the synthesis step remains in the system during the post-treatment step subsequent to the synthesis step. The operations of the "synthesis step" and the "post-treatment step" are accordingly relevant to the subsequent first step. Hence, the "synthesis step" and the "post-treatment step" will be generally explained below, and then, the "first step" and the "polymerization step (second step)" will be explained below in detail.

[Synthesis Step of Fluorine-Containing Polymerizable Monomer of Formula (1) (Also Simply Referred to as "Synthesis Step")]

The fluorine-containing polymerizable monomer of the formula (1) can be synthesized by condensation reaction between an alcohol of the formula (6) and a polymerizable double bond-containing carboxylic acid, carboxylic acid halide, carboxylic acid ester or carboxylic anhydride compound of the formula (5) as shown in the following scheme 2.

Scheme 2

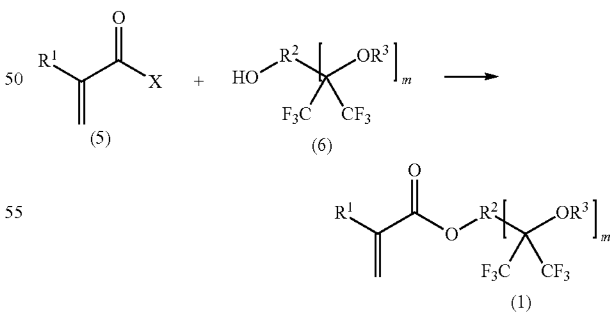

In the above formulas, X is a hydroxy group, a halogen atom, an alkoxy group, or an oxocarbonyl group; and the definitions of other symbols are the same as in the formula (1). As the halogen atom, fluorine or chlorine is often used. Examples of the alkoxy group include those of 1 to 6 carbon atoms. Examples of the oxocarbonyl group include those represented by $R^1(C{=}C)$—$(C{=}O)O$. In particular, the oxocarbonyl group in which $R^1$ is the same as $R^1$ on the left side of the formula (5) is often used as an acid anhydride. As mentioned above, this synthesis step itself is a known literature reaction (see Patent Documents 7 and 8 for the details thereof).

The compound of the formula (5) can be selected depending on the structure of the target fluorine-containing polymerizable monomer. In the present specification, the compound of the formula (5) in which $R^1$ is hydrogen is referred to as an "acrylating agent"; the compound of the formula (5) in which $R^1$ is methyl is referred to as a "methacrylating agent"; the compound of the formula (5) in which $R^1$ is fluorine is referred to as a "2-fluoroacrylating agent"; and the compound of the formula (5) in which $R^1$ is trifluoromethyl is referred to as a "2-trifluoromethylacrylating agent".

Examples of the acrylating agent include: acrylic acid esters such as methyl acrylate, ethyl acrylate, n-propyl acrylate, iso-propyl acrylate, n-butyl acrylate, iso-butyl acrylate, sec-butyl acrylate and tert-butyl acrylate; acid halides such as acrylic acid chloride, acrylic acid fluoride and acrylic acid bromide; acrylic anhydride; and acrylic acid. Examples of the methacrylating agent include: methacrylic acid esters such as methyl methacrylate, ethyl methacrylate, n-propyl methacrylate, iso-propyl methacrylate, n-butyl methacrylate, iso-butyl methacrylate, sec-butyl methacrylate and tert-butyl methacrylate; acid halides such as methacrylic acid chloride, methacrylic acid fluoride and methacrylic acid bromide; methacrylic anhydride; and methacrylic acid. Examples of the 2-fluoroacrylating agent include: 2-fluoroacrylic acid esters such as methyl 2-fluoroacrylate; ethyl 2-fluoroacrylate, n-propyl 2-fluoroacrylate, iso-propyl 2-fluoroacrylate, n-butyl 2-fluoroacrylate, iso-butyl 2-fluoroacrylate, sec-butyl 2-fluoroacrylate and tert-butyl 2-fluoroacrylate; acid halides such as 2-fluoroacrylic acid chloride, 2-fluoroacrylic acid fluoride and 2-fluoroacrylic acid bromide; 2-fluoroacrylic anhydride; and 2-fluoroacrylic acid. Examples of the 2-trifluoromethylacrylating agent include: 2-trifluoromethylacrylic acid esters such as methyl 2-trifluoromethylacrylate, ethyl 2-trifluoromethylacrylate, n-propyl 2-trifluoromethylacrylate, iso-propyl 2-trifluoromethylacrylate, n-butyl 2-trifluoromethylacrylate, iso-butyl 2-trifluoromethylacrylate, sec-butyl 2-trifluoromethylacrylate and tert-butyl 2-trifluoromethylacrylate; acid halides such as 2-trifluoromethylacrylic acid chloride, 2-trifluoromethylacrylic acid fluoride and 2-trifluoromethylacrylic acid bromide; 2-trifluoromethylacrylic anhydride; and 2-trifluoromethylacrylic acid.

Among others, (meth)acrylic anhydride and (meth)acrylic acid chloride are preferred because of the facts that: these compounds show high reactivity in the reaction of the above scheme 1; and the resulting fluorine-containing polymerizable monomer shows good polymerizability, as disclosed in Patent Documents 6 and 7.

The following compounds are specific examples of the alcohol of the formula (6).

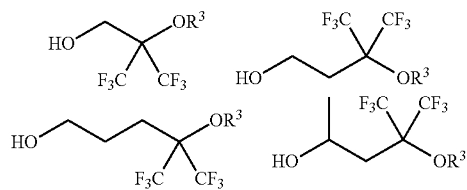

-continued

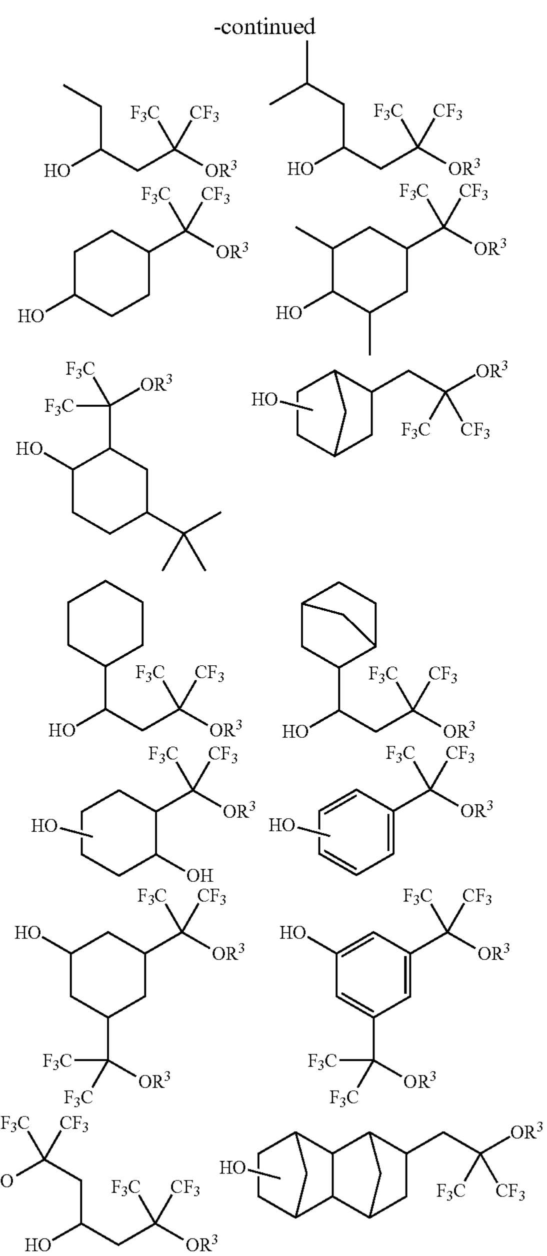

As the substituent group $R^3$ in the alcohol of the formula (3), there can be used not only an alkyl or fluoroalkyl group such as hydrogen, methyl, ethyl, n-propyl, iso-propyl, n-butyl, iso-butyl, tert-butyl, 2,2,2-trifluoroethyl, 3,3,3-trifluoro-n-propyl or hexafluoroisopropyl, but also a protecting group that can be easily deprotected by an acid or base, such as methoxymethyl, ethoxymethyl, methoxyethyl, methoxyisopropyl, acetyl, tert-butoxycarbonyl and trialkylsilyl. In the case of m=2, two $R^3$ may be of the same kind or of different kinds.

It is preferable that this synthesis step takes place in the presence of a phenolic polymerization inhibitor (also called a hydroquinone-based polymerization inhibitor) such as hydroquinone, methoquinone, 1,2,4-trihydroxybenzene etc. or a nitrogen-containing polymerization inhibitor such as phenothiazine, 1-diphenyl-2-picrylhydrazyl, Nonflex F (N,N'-di-2-naphthyl-para-phenylenediamine) etc. because the target fluorine-containing polymerizable monomer tends to be stably obtained with high yield by the use of such a polymerization inhibitor as disclosed in Patent Documents 7 and 8. The amount of the polymerization inhibitor used (in the case of using a plurality of kinds of polymerization inhibitors, the total amount of the polymerization inhibitors used) is generally 0.005 to 3 parts by mass, preferably 0.01 to 2 parts by mass, more preferably 0.01 to 1 part by mass, per 100 parts by mass of the alcohol of the formula (6).

In the synthesis step, the reaction proceeds under relatively moderate conditions as will be explained below. Thus, the frequency of occurrence of polymerization as a side reaction in the synthesis step is much lower than in the distillation purification step (first step). In addition, the problem of "device clogging", which can arise in the distillation purification step, is limitative in the synthesis step. For these reasons, there is no particular limitation on the selection of the polymerization inhibitor in the synthesis step of the fluorine-containing polymerizable monomer of the formula (1).

There is a tendency that, once a polymerization inhibitor is added to the reaction system, a part of the added polymerization inhibitor remains in the system even though the "post-treatment step (typically including water washing)" takes place after the reaction. Depending on the kind of the polymerization inhibitor, the polymerization inhibitor may remain until distillation of the fluorine-containing polymerizable monomer of the formula (1) and cause a coloring phenomenon during the distillation as mentioned in the beginning section of the present specification (see also the after-mentioned Comparative Example 1-3). With a view to suppression of such coloring, it is preferable to use the "phenolic compound (hydroquinone derivative)" as the polymerization inhibitor (i.e. not to use a nitrogen-containing polymerization inhibitor) in the synthesis step. This makes it easy to benefit from the advantage of the phenolic polymerization inhibitor, which is the less likelihood of coloring, in the subsequent distillation purification step (first step).

More specifically, it is particularly preferable to use at least one kind selected from the phenolic compounds A and B as the polymerization inhibitor in the synthesis step. There would be no hindrance even when the synthesis step takes place with the addition of both of the phenolic compounds A and B. However, polymerization is relatively unlikely to occur as a side reaction in the synthesis step as mentioned above. In the case of performing washing operation (water washing) after the synthesis reaction, a part of the phenolic compound is dissolved in water and discharged to the outside of the reaction system. It is thus not necessarily required to use both of the phenolic compounds A and B in the synthesis step. The synthesis step may be conducted by using either one of the phenolic compounds A and B (e.g. using the generally easily available phenolic compound A).

The reaction can be carried out under either acidic conditions or basic conditions. Examples of an acid catalyst usable in the reaction include: inorganic acids such as sulfuric acid, hydrochloric acid, phosphoric acid, zinc chloride and titanium tetrachloride; and organic acids such as methanesulfonic acid, trifluoromethanesulfonic acid, benzenesulfonic acid and p-toluenesulfonic acid. These acid catalysts can be used solely or as a mixture of two or more thereof. Examples of a base catalyst usable in the reaction include ammonia, pyridine, 2,6-lutidine, triethylamine, 1,8-diazabicyclo[5.4.0]undecene-7, N,N'-dimethyl-4-aminopyridine, lithium hydride, sodium hydride and potassium hydride. These base catalysts can be used solely or as a mixture of two or more thereof.

There is no particular limitation on the amount of the acid catalyst or base catalyst used in the synthesis step. It is preferable to use the acid catalyst in an amount of 0.01 to 2 mol, or use the base catalyst in an amount of 0.5 to 3 mol, per 1 mol of the alcohol of the formula (6).

There is no particular limitation on the reaction temperature in the synthesis step. In the case of using the acid catalyst, the reaction temperature can be set within the range of e.g. 0 to +80° C. by those skilled in the art. In the case of using the base catalyst, the reaction temperature can be set within the range of e.g. −20 to +100° C. by those skilled in the art.

There is no particular limitation on the kind of the reaction solvent in the synthesis step as long as the reaction solvent is not involved in the condensation reaction.

As the reaction solvent, hydrocarbons, aromatic hydrocarbons, ketones, ethers, hydrofluorocarbons, hydrofluoroethers and the like are usable. Although the reaction can be carried out in the absence of the reaction solvent, it is preferable to use the reaction solvent in terms of control of the reaction temperature and handling of the reaction solution.

Examples of the hydrocarbon solvents include butane, pentane, hexane, heptane, octane, nonane and decane. Examples of the aromatic hydrocarbon solvents include benzene, toluene, xylene, mesitylene and perfluorobenzene. Examples of the ketone solvents include acetone, methyl ethyl ketone, diethyl ketone, methyl n-propyl ketone, methyl iso-propyl ketone, methyl n-butyl ketone and methyl isobutyl ketone. Examples of the ether solvents include diethyl ether, methyl t-butyl ether, diisopropyl ether, dibutyl ether and tetrahydrofuran. Examples of the hydrofluorocarbon solvents include trifluoromethane, difluoromethane, 1,1,1,2-tetrafluoroethane, 1,1,1-tetrafluoroethane, 1,1-difluoroethane, 1,1,1,2,3,3,3-heptafluoropropane, 1,1,1,3,3,3-hexafluoropropane, 1,1,1,3,3-heptafluoropropane, 1,1,1,3,3-pentafluorobutane, 1,1,1,2,2,3,4,5,5,5-decafluoropentane and 1,1,2,2,3,3,4-heptafluorocyclopentane.

Examples of the hydrofluoroether solvents include (methyl)(1,1,2,2,2-pentafluoroethyl)ether, (methyl)(trifluoromethyl)ether, (methyl)(1,1,2,2-tetrafluorethyl)ether, 1,1,2,2-tetrafluoro-1-(2,2,2-trifluoroethoxy)ethane, (2,2,3,3-tetrafluoropropyl)(1,1,2,3,3,3-hexafluoropropyl)ether, (methyl)(nonafluorobutyl)ether, (methyl)(nonafluoroisobutyl)ether, (ethyl)(nonafluorobutyl)ether, (ethyl)(nonafluoroisobutyl)ether, 1,1,1,2,2,3,4,5,5,5-decafluoro-3-methoxy-dodecafluorohexane and 1,1,1,2,3-hexafluoro-4-(1,1,2,3,3,3-hexafluoropropoxy)pentane. The above solvents can be used solely or as a mixture of two or more thereof.

[Post-Treatment Step]

After the completion of the "synthesis step", the resulting reaction mixture can be subjected to the "post-treatment step". The post-treatment step refers to an operation of water washing, filtration, concentration (e.g. evaporation or flash distillation) etc. Any arbitrary post-treatment operation can be selected and performed. Among others, water washing and concentration are particularly useful.

Although the "post-treatment step" is not essential, it is feasible by the post-treatment step to remove the residue of the acid catalyst or base catalyst used in the "synthesis step" and to remove the reaction solvent so that the load of distillation equipment in the subsequent distillation purification step (first step) can be reduced. It is thus preferable to conduct the "post-treatment step" after the completion of the "synthesis step" and before the initiation of the first step.

There is no particular limitation on the operation procedure of the post-treatment step. For example, "water washing" can be preferably performed by adding 0.5 to 10 g of water per 1 g of the reaction mixture obtained in the "synthesis step", stirring the mixture well, leaving the mixture still and then separating the mixture into two layers. It is effective to repeat this "water washing operation" two or three times.

The water washing may be performed in the coexistence of an inorganic base such as sodium carbonate, sodium hydrogencarbonate, potassium carbonate or potassium hydrogencarbonate. The water washing may alternatively performed with the use of pure water (including industrial water).

In the case where the phenolic compound A or phenolic compound B is used as the polymerization inhibitor in the synthesis step, the phenolic compound is gradually washed away by water during the water washing operation as mentioned above because of its water solubility. When the water washing operation is repeated two or three times, it is typical that: 10% to 50% of the polymerization inhibitor used in the synthesis step is washed by water; and 50% to 90% of the polymerization inhibitor used in the synthesis step remains in the reaction mixture.

By performing evaporation (condensation) after the water washing, the solvent used in the synthesis step, the remaining raw material compounds of the formulas (5) and (6) and by-products of low boiling points can be removed.

In the case where any solid substance such as solid catalyst used in the condensation reaction, salt derived from the base used in the condensation reaction or by-produced polymer is present in the system, the solid substance can be removed by filtration.

The fluorine-containing polymerizable monomer obtained by the above-mentioned "post-treatment step" is usable as a raw material in the "distillation purification step (first step)". The filter used in the filtration operation and the method of the filtration operation are not particularly limited.

[Distillation Purification Step (First Step)]

The "distillation purification step (also called the first step)" is a step of distilling the fluorine-containing polymerizable monomer of the formula (1) in the presence of the phenolic compound A and the phenolic compound B.

In the above-mentioned "post-treatment step", the purity of the fluorine-containing polymerizable monomer is increased to a certain level. In the first step, the distillation purification is performed to, in the case where a component of high boiling point or an impurity of close boiling point is present, remove such an impurity component and thereby significantly improve the quality reliability of the fluorine-containing polymerizable monomer.

The present invention is characterized in that the fluorine-containing polymerizable monomer is distilled in the coexistence of the phenolic compound A and the phenolic compound B in the first step. By this operation, polymer forming reaction (polymerization or oligomerization) of the polymerizable monomer including the fluorine-containing polymerizable monomer of the formula (1) is significantly suppressed during the distillation.

Basically, the distillation conditions (such as distillation temperature, plate number, reflux ratio etc.) of the first step are varied depending on not only the kind, impurity profile and boiling point of the polymerizable monomer to be distilled, but also the purification degree required of the target compound (fraction). In the case where the distillation conditions are moderate, polymerization is less likely to occur during the distillation. In the case where the distillation conditions are severe (e.g. where more strict distillation is required because of the high boiling point of the polymerizable monomer or the presence of close boiling point impurity), polymerization is likely to occur during the distillation. Further, the likelihood of occurrence of polymerization during the distillation varies depending on the kind of the polymerizable monomer.

It is however an important point that, regardless of whether or not the distillation conditions are likely to cause polymerization, the occurrence of polymerization during the distillation is relatively significantly suppressed to allow an improvement in distillation operability by performing the distillation in the coexistence of the phenolic compound A and the phenolic compound B in the first step of the present invention. The distillation step is thus improved in operability. This effect can also be confirmed from the evidence that the coexistence of the phenolic compounds A and B allows a significant reduction of polymerization during the distillation, as compared to the case of using only the phenolic compound A or B as the polymerization inhibitor while making the other conditions exactly the same, (which will be verified by the after-mentioned Examples and Comparative Examples).

Preferable examples of the phenolic compounds A and B and more preferable examples of the phenolic compounds A and B are as mentioned above.

In the first step (distillation purification step), the use of a plurality of kinds of phenolic compounds A or a plurality of kinds of phenolic compounds B would not be excluded. However, the use of an increased number of kinds of phenolic compounds does not contribute to a remarkable increase of polymerization inhibiting effect and results in complicated management. The combined use of one kind of phenolic compound A and one kind of phenolic compound B is thus particularly preferred as mentioned above.

In the distillation purification step, a third polymerization inhibitor (such as nitrogen-containing polymerization inhibitor) other than the phenolic compounds A and B may be further added. In this case, however, the quality management becomes complicated. Further, there is seen no effect of the addition of the third or more polymerization inhibitors. It suffices to use only the above-mentioned two kinds of phenolic compounds A and B.

The amount of the phenolic compounds A and B contained as the polymerization inhibitors in the crude product of the fluorine-containing polymerizable monomer of the formula (1) immediately before the distillation is generally 0.01 to 5 parts by mass, preferably 0.01 to 1 parts by mass, per 100 parts by mass of the crude product of the fluorine-containing polymerizable monomer of the formula (1). When the amount of the phenolic compounds A and B contained in the crude product is less than 0.01 parts by mass, the effect of these polymerization inhibitor compounds may not be sufficient. By contrast, there may arises an economic burden when the amount of the phenolic compounds A and B contained in the crude product exceeds 5 parts by mass. It is unfavorable that the amount of the polymerization inhibitors contained in the polymerizable monomer is too large because, in such a case, the polymerization inhibitors may inhibit polymerization reaction in the subsequent polymerization step and thus need to be removed by performing another operation step after the completion of the distillation step.

It is preferable that the mass ratio of the phenolic compound A and the phenolic compound B is in the range of 1:0.1 to 1:10 in the first step because, in such a mass ratio range, the effect of the combined use of the phenolic compounds A and B is enhanced. It is particularly preferable that the mass ratio of the phenolic compound A and the phenolic compound B is in the range of 1:0.2 to 1:2. When the mass ratio of the phenolic compound A and the phenolic compound B is out of the above range, the effect of the combined use of these two phenolic compounds may become insufficient.

There is no particular limitation on the adjustment method of the content amounts of the phenolic compounds A and B. In the case where the phenolic compound is not contained at all in the fluorine-containing polymerizable monomer, the phenolic compounds A and B can be added in predetermined mass amounts relative to the mass of the fluorine-containing polymerizable monomer.

In the case where the phenolic compound A or B is already added as the polymerization inhibitor in the synthesis step, it is usual that a part of the polymerization inhibitor (typically 50% to 90% of the polymerization inhibitor added in the synthesis step) remains in the fluorine-containing polymerizable monomer. In such a case, the amount of the polymerization inhibitor contained is adjusted by e.g. the following procedure.

Using known samples, a correlation coefficient between the amount of the phenolic compound A, B and the intensity of the gas chromatogram peak is calculated in advance by gas chromatography. Then, a gas chromatogram of the fluorine-containing polymerizable monomer of the formula (1) before the distillation, as obtained through the above-mentioned synthesis and post-treatment steps, is measured by the same apparatus as that used for calculation of the correlation coefficient. The amount of the phenolic compound A or B already contained in the fluorine-containing polymerizable monomer of the formula (1) before the distillation is determined based on the peak intensity of the phenolic compound A or B in the measured gas chromatogram. The amount of the phenolic compound A or B added immediately before the distillation is determined as a shortage amount by subtracting the "amount of the phenolic compound already contained" from the above-mentioned "amount of the phenolic compound contained immediately before the distillation".

By the above procedure, the mass ratio of the phenolic compounds A and B is adjusted to a desired value (e.g. 1:1) immediately before the distillation even when either one of the phenolic compounds A and B is contained in the fluorine-containing polymerizable monomer or when the amount of the phenolic compound A or B contained in the fluorine-containing polymerizable monomer is smaller than a predetermined value.

The pressure during the distillation purification operation of the first step is preferably set depending on the boiling point of the fluorine-containing polymerizable monomer of the formula (1). In the case of performing the distillation under reduced pressure, the distillation temperature is limited to prevent unexpected decomposition reaction and to save energy as compared to the case of performing the distillation under atmospheric pressure. The distillation temperature (bottom liquid temperature) is generally 50 to 250° C., preferably 80 to 180° C. It is preferable to perform the distillation by setting the reduced pressure condition such that the fluorine-containing polymerizable monomer can be distilled in the above temperature range.

The distillation equipment is selected depending on the composition of the crude product of the fluorine-containing polymerizable monomer of the formula (1), that is, depending on the amount of by-products that need to be separated. As the distillation equipment, there can be used a short pass distillation apparatus such as thin-film distillation apparatus, a simple distillation apparatus or a distillation apparatus with a distillation column. In the case of using the distillation column, there is no particular limitation on the plate number of the distillation column. The plate number of the distillation column is generally 1 to 40, preferably 2 to 20. The impurity separating/removing performance of the distillation column is increased as the plate number of the distillation column is larger. On the other hand, the distillation column is disadvantageous in terms of the energy efficiency when the plate number of the distillation column exceed 40.

Further, there is no particular limitation on the lower limit of the plate number of the distillation equipment. However, the polymerization inhibitors used in the first step of the present invention tend to exert their effect under severe distillation conditions where the plate number of the distillation column is relatively large. It is thus preferable to use the distillation column with a plate number of 2 or more, more preferably 3 or more, rather than to use the distillation column with a plate number of 1, in terms of the merit of the application of the polymerization inhibitors in the present invention.

There is also no particular limitation on the reflux ratio of the distillation column. The reflux ratio is generally in the range of 1:1 to 1:50, preferably 1:1 to 1/20.

The distillation purification operation of the first step may be performed, as so-called aeration distillation, while flowing oxygen gas or diluted oxygen gas (i.e. oxygen diluted with inert gas such as nitrogen or argon) through the distillation vessel. By this operation, the effect of the polymerization inhibitors is further enhanced.

Many kinds of the phenolic compounds A and B are solid. Each of these solid phenolic compounds has sublimability so that, depending on the distillation conditions in the first step, a part of the solid phenolic compound (in general, 0.005 to 0.1 parts by mass of the phenolic compound A and 0 to 0.01 parts by mass of the phenolic compound B) is entrained in the distillation fraction. As a matter of importance, however, the phenolic polymerization inhibitor, when contained in the above content range, does not interfere with polymerization under the conditions of the subsequent "polymerization step (second step)". Furthermore, the phenolic compound contained in the distillation fraction largely contributes to the storage stability of the fluorine-containing polymerizable monomer after the distillation (more specifically, the storage stability of the fluorine-containing polymerizable monomer from the completion of the first step until the initiation of the second step). There is thus usually no need to remove the phenolic compound from the distillation fraction. For even phenolic compound contents between production lots, it is preferable to analyze the amounts of the respective phenolic compounds A and B contained in the distillation fraction, newly add the phenolic compounds A and B as required and thereby control the content amounts of the phenolic compounds A and B to predetermined values.

[Polymerization Step (Second Step)]

The "polymerization step (second step)" is a step of polymerizing the fluorine-containing polymerizable monomer obtained with a high purity by the first step, thereby forming a fluorine-containing polymer with a repeating unit of the above general formula (4).

In the present invention, the fluorine-containing polymerizable monomer of the formula (1) has self polymerizability and thus, in the absence of any other polymerizable monomer, form a homopolymer having a single kind of repeating unit of the formula (4) at a high yield. On the other hand, the fluorine-containing polymerizable monomer of the formula (1) forms a heteropolymer (also referred to as fluorine-containing copolymer) by copolymerization with a wide variety of other polymerizable monomer (e.g. C=C double bond-containing compound) at an arbitrary ratio. Even in this case, a homopolymer of the fluorine-containing polymerizable monomer of the formula (1) may be partially formed in the system. In the present invention, the "fluorine-containing polymer with the repeating unit of the formula (4)" refers to any of polymers (homopolymer and heteropolymer) in general formed using the fluorine-containing polymerizable monomer of the formula (1).

In the second step (polymerization step), the fluorine-containing polymerizable monomer of the formula (1) is reacted for a predetermine time at a predetermined temperature by contact with a polymerization initiator. When the target compound is a heteropolymer, the second step is conducted in a state that the fluorine-containing polymerizable monomer of the formula (1) coexists with any other polymerizable monomer (also simply referred to as "other polymerizable monomer" in the present specification). As the polymerization initiator, a radical initiator is used in a radical polymerization process; a proton acid or a Lewis acid is used in a cationic polymerization process; and an organic metal complex is used in an anionic polymerization process. In the polymerization step of the present invention, a radical polymerization process is particularly preferred.

In general, the fluorine-containing polymerizable monomer of the formula (1) used as a raw material in the second step (polymerization step) contains a trace amount of the polymerization inhibitor A and/or B used in the above-mentioned first step (distillation step). From the perspective of maintaining a constant quality of the fluorine-containing polymer obtained in the second step, it is preferable to determine the amounts of the polymerization inhibitors contained in the raw material monomer by process analysis and add the phenolic compounds A and B to the raw material monomer such that the amounts of the phenolic compounds A and B contained in the raw material monomer are respectively controlled to within predetermined levels. More specifically, the amounts of the phenolic compounds are preferably determined and controlled by process analysis such that the amount of the phenolic compound A contained is in the range of 0.05 to 0.2 parts by mass and the amount of the phenolic compound B contained is in the range of 0.05 to 0.1 parts by mass per 100 parts by mass of the fluorine-containing polymerizable monomer of the formula (1). As the polymerization inhibiting effect of the polymerization inhibitors is promptly lost by the addition of the polymerization initiator in the second step, the fluorine-containing polymer is smoothly formed (see the after-mentioned Examples 5 and 6).

The "other polymerizable monomer" can be one or more kinds of monomers selected from a fluorine-containing polymerizable monomer of the formula (1) in which at least one of $R^1$, $R^2$, $R^3$ and m is varied, acrylic acid esters, fluorine-containing acrylic acid esters, methacrylic acid esters, fluorine-containing methacrylic acid esters, styrenic compounds, fluorine-containing styrenic compounds, fluorine-containing vinyl ethers, allyl ethers, fluorine-containing allyl ethers, unsaturated amides, olefins, fluorine-containing olefins, norbornenes, fluorine-containing norbornenes, vinyl silanes, vinyl sulfones, vinylsulfonic acid esters, acrylic acid, methacrylic acid, maleic acid, maleic anhydride and fumaric acid.

Examples of the acrylic acid esters include methyl acrylate, ethyl acrylate, n-propyl acrylate, isopropyl acrylate, n-butyl acrylate, isobutyl acrylate, n-hexyl acrylate, n-octyl acrylate, 2-ethylhexyl acrylate, lauryl acrylate, 2-hydroxyethyl acrylate, 2-hydroxypropyl acrylate, tert-butyl acrylate, 3-oxocyclohexyl acrylate, adamantyl acrylate, methyladamantyl acrylate, ethyladamantyl acrylate, hydroxyadamantyl acrylate, cyclohexyl acrylate and tricyclodecanyl acrylate.

Examples of the methacrylic acid esters include methyl methacrylate, ethyl methacrylate, n-propyl methacrylate, isopropyl methacrylate, n-butyl methacrylate, isobutyl methacrylate, n-hexyl methacrylate, n-octyl methacrylate, 2-ethylhexyl methacrylate, lauryl methacrylate, 2-hydroxyethyl methacrylate, 2-hydroxypropyl methacrylate, tert-butyl methacrylate, 3-oxocyclohexyl methacrylate, adamantyl methacrylate, methyladamantyl methacrylate, ethyladamantyl methacrylate, hydroxyadamantyl methacrylate, cyclohexyl methacrylate and tricyclodecanyl methacrylate.

The "other polymerizable monomer" may be an acrylate or methacrylate having an ethylene glycol, propylene glycol or tetramethylene glycol structure, or may be an acrylate or methacrylate having a ring structure such as lactone ring or norbornene ring. The "other polymerizable monomer" may be acrylonitrile, methacrylonitrile, an acrylic acid having an alkoxysilane structure, or vinyl silane.

Next, the fluorine-containing acrylic acid esters and fluorine-containing methacrylic acid esters usable as the "other polymerizable monomer" will be explained below. More specifically, the fluorine-containing acrylic or methacrylic acid ester can be an acrylic acid ester having a fluorine atom or a fluorine-containing alkyl group in the α-position of the acrylic moiety, or an acrylic or methacrylic acid ester having a fluorine atom or fluorine-containing alkyl group in the ester moiety.

In the fluorine-containing acrylic or methacrylic acid ester, fluorine atoms or fluoroalkyl groups may be introduced to both of the α-position of the acrylic moiety and the ester moiety.

As the fluoroalkyl group introduced to the α-position of the acrylic moiety of the fluorine-containing acrylic or methacrylic acid ester, there can be used trifluoromethyl, trifluoroethyl or nonafluoro-n-butyl.

In the fluorine-containing acrylic or methacrylic acid ester, the ester moiety may include a fluorinated alkyl group such as perfluoroalkyl group or fluoroalkyl group. Further, a cyclic structure and a fluorine atom may coexist in the ester moiety of the fluorine-containing acrylic or methacrylic acid ester. In such a case, the cyclic structure may contain a fluorine-containing benzene ring, a fluorine-containing cyclopentane ring, a fluorine-containing cyclohexane ring or a fluorine-containing cycloheptane ring, each of which having a fluorine atom, a trifluoromethyl group, a hexafluoroisopropylhydroxy group etc.

Examples of the fluorine-containing acrylic acid esters include 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, perfluorocyclohexylmethyl acrylate, 6-[3,3,3-trifluoro-2-hydroxy-2-(trifluoromethyl)propyl]bicyclo[2.2.1]hept-2-yl acrylate, 6-[3,3,3-trifluoro-2-hydroxy-2-(trifluoromethyl)propyl]bicyclo[2.2.1]hept-2-yl-2-(trifluoro methyl) acrylate, 3,5-bis(1,1,1,3,3,3-hexafluoro-2-hydroxyisopropyl)cyclohexyl-2-trifluoromethyl acrylate, and 2-(perfluorohexyl)ethyl acrylate.

Examples of the fluorine-containing methacrylic acid esters include 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl methacrylate, 6-[3,3,3-trifluoro-2-hydroxy-2-(trifluoromethyl)propyl]bicyclo[2.2.1]hept-2-yl methacrylate, 3,5-bis(1,1,1,3,3,3-hexafluoro-2-hydroxyisopropyl)cyclohexyl acrylate, 3,5-bis(1,1,1,3,3,3-hexafluoro-2-hydroxyisopropyl)cyclohexyl methacrylate and 2-(perfluorohexyl)ethyl methacrylate.

Examples of the styrenic compounds and fluorine-containing styrenic compounds usable as the “other polymerizable monomer” include styrene, fluorinated styrenes and hydroxystyrenes.

For instance, there can be used: a styrene in which a hydrogen atom on the aromatic ring has been replaced by a fluorine atom or trifluoromethyl group, such as pentafluorostyrene, trifluoromethylstyrene or bistrifluoromethylstyrene; and a styrene in which a hydrogen atom on the aromatic ring has been replaced by a hexafluoroisopropanol group or hydroxyl-protected hexafluoroisopropanol group. In the above-mentioned styrene, a halogen atom, alkyl group or fluoroalkyl group may be bonded to the α-position. There can also be used a styrene containing a perfluorovinyl group.

Examples of the vinyl ethers, the fluorine-containing vinyl ethers, the allyl ethers and the fluorine-containing allyl ethers usable as the “other polymerizable monomer” include: those containing a methyl group, an ethyl group, a propyl group, a butyl group or a hydroxy group such as hydroxyethyl or hydroxybutyl in its structure; and those containing a cyclohexyl group, a norbornyl group, an aromatic ring group or a cyclic vinyl or allyl ether group having a hydrogen or carbonyl bond in its cyclic structure. A part or all of hydrogen atoms of these ether compounds may be substituted with a fluorine atom.

Examples of the unsaturated amides usable as the “other polymerizable monomer” include acrylamide, methacrylamide, N-methylolacrylamide, N-methylolmethacrylamide and diacetone acrylamide.

Examples of the olefins usable as the “other polymerizable monomer” include ethylene, propylene, cyclopentene and cyclohexene. Examples of the fluorine-containing olefins usable as the “other polymerizable monomer” include vinyl fluoride, vinlidene fluoride, trifluoroethylene, chlorotrifluoroethylene, tetrafluoroethylene, hexafluoropropylene and hexafluoroisobutene.

The above-mentioned “other polymerizable monomers” may be used alone, or in combination of two or more kinds thereof, for copolymerization with the fluorine-containing polymerizable monomer of the formula (1).

In the case where the fluorine-containing polymer with the repeating unit of the formula (4) is a copolymer of the fluorine-containing polymerizable monomer (formula (1)) and the other polymerizable monomer, the proportion of the repeating unit formed by cleavage of the fluorine-containing polymerizable monomer to the repeating unit formed by cleavage of the other polymerizable monomer in the fluorine-containing copolymer can be set with no particular limitation. For example, the ratio of the number of repeating units derived from the fluorine-containing polymerizable monomer of the formula (1) relative to the total number of repeating units contained in the fluorine-containing polymer can be set 1 to 99.9%. It is feasible to set the repeating unit ratio by adjusting the composition of the respective monomer components charged in the second step.

As already mentioned above, the fluorine-containing polymerizable monomer of the formula (1) has self polymerizability, and thus can form a straight chain by homopolymerization thereof. In the presence of the other polymerizable monomer, however, the fluorine-containing polymerizable monomer of the formula (1) can form a copolymer with the other polymerizable monomer by incorporating the other polymerizable monomer in the main chain of the copolymer. This is the reason why the proportion of the repeating fluorine-containing polymerizable monomer unit of the formula (1) in the fluorine-containing polymer is in a wide range of 1 to 99.9%. Among others, it is preferable that the proportion of the repeating fluorine-containing polymerizable monomer unit of the formula (1) in the fluorine-containing polymer is 50% or higher so that the polymer readily reflects good physical properties of the repeating fluorine-containing polymerizable monomer unit of the formula (1). On the other hand, it is not excluded that the “other polymerizable monomer” is added in a very small amount, as if as an additive, to improve some physical properties of the fluorine-containing polymer There is thus no particular limitation on the upper limit of the proportion of the repeating fluorine-containing polymerizable monomer unit of the formula (1). Although it is conceivable that the proportion of the repeating fluorine-containing polymerizable monomer unit of the formula (1) exceeds 99.9%, the proportion of the other polymerizable monomer unit is very low in such a case so that the technical significance to add the other polymerizable monomer becomes small.

In the case where the proportion of the repeating unit derived from the fluorine-containing polymerizable monomer of the formula (1) exceeds 90%, a homopolymer of the fluorine-containing polymerizable monomer of the formula (1) and a copolymer of the fluorine-containing polymerizable monomer of the formula (1) and the other polymerizable monomer may be microscopically present in a mixed state to thereby form one resin composition. All of these are included in the fluorine-containing polymer of the present invention.

Next, a method for producing the fluorine-containing polymer or copolymer with the repeating unit of the formula (4) by polymerization or copolymerization with the other polymerizable monomer will be explained below.

The production method is not particularly limited as long as it utilizes a common polymerization reaction process. In the production method, a radial polymerization process or an ionic polymerization process is preferred. In some cases, a coordinated anionic polymerization process, a living anionic polymerization process or a cationic polymerization process may be used. Among others, a radial polymerization process is particularly preferred because the radial polymerization process is especially convenient in operation and allows high-yield production of the target fluorine-containing polymer from the fluorine-containing polymerizable monomer of the formula (1) by the use of a general-purpose radial polymerization initiator. Hence, an explanation of the radial polymerization process will be given below.

In the production method of the fluorine-containing polymer or copolymer with the repeating unit of the formula (4), the radical polymerization process can be performed in the presence of a radial polymerization initiator in a known polymerization system such as bulk polymerization system, solution polymerization system, suspension polymerization system or emulsion polymerization system by batch operation, semi-continuous operation or continuous operation. It is needless to say that it is preferable to carry out the polymerization reaction while stirring well the inside of the reactor and measuring the heat of reaction.

There is no particular limitation on the kind of the radial polymerization initiator used. As the radial polymerization initiator, an azo compound, a peroxide compound and a redox compound are usable. In the case of a living radical polymerization process, any corresponding reagent can be added.

Examples of the azo compound usable as the radial polymerization initiator includes 2,2'-azobis(isobutyronitrile), dimethyl 2,2'-azobis(isobutyrate), 2,2'-azobis(4-methoxy-2,4-dimethylvaleronitrile), 2,2'-azobis(2,4-dimethylvaleronitrile), 2,2'-azobis(2-methylbutyronitrile), 1,1'-azobis(cyclohexane-1-carbonitrile), 2,2'-azobis[2-(2-imidazolin-2-yl)propane], 2,2'-azobis(2-methylpropionamidine) dihydrochloride, 2,2'-azobis[2-methyl-N-(2-hydroxyethyl)propionamide], 2,2'-azobis[N-(2-propenyl)-2-methylpropionamide] and 4,4'-azobis(4-cyanovaleric acid). Examples of the peroxide compound usable as the radial polymerization initiator include t-butyl peroxypivalate, di-t-butyl peroxide, i-butyryl peroxide, lauroyl peroxide, succinic acid peroxide, cinnamyl peroxide, di-n-propyl peroxydicarbonate, benzoyl peroxide, hydrogen peroxide and ammonium persulfate.

For reversible addition-fragmentation chain transfer (RAFT) polymerization, which is one type of living radical polymerization, a dithiobenzoate compound, a trithiocarbonate compound, a dithiocarbamate compound, a xanthate compound etc. is added as a RAFT reagent. Examples of the RAFT reagent include 2-cyano-2-propyl benzodithioate, 4-cyano-4-[(dodecylsulfanylthiocarbonyl)sulfanyl]pentanoic acid, cyanomethyl methyl(phenyl)carbamodithioate, 4-cyano-4-(phenylcarbonothioylthio)pentanoic acid, 2-cycano-2-propyl dodecyl trithiocarbonate, 2-(dodecylthiocarbonothioylthio)-2-methylpropionic acid and cyanomethyl dodecyl trithiocarbonate.

There is no particular limitation on the reactor used in the polymerization process. The polymerization process may be performed with the use of a solvent.

There is also no particular limitation on the kind of the polymerization solvent used as long as the polymerization solvent does not interfere with the radical polymerization reaction. The polymerization solvent can be selected from hydrocarbon solvents, ester solvents, ketone solvents, alcohol solvents, ether solvents, cyclic ether solvents, fluorocarbon solvents, aromatic solvents and water. These solvents can be used solely or as a mixture of two or more kinds thereof.

Examples of the polymerization solvents include: ester solvents such as ethyl acetate and n-butyl acetate; ketone solvents such as acetone and methyl isobutyl ketone; hydrocarbon solvents such as toluene and cyclohexane; and alcohol solvents such as methanol, isopropyl alcohol and ethylene glycol monomethyl ether.

In the radical polymerization process, a molecular weight modifier such as mercaptan may be used. The reaction temperature in the radical polymerization process can be set as appropriate depending on the kind of the radical polymerization initiator or radical polymerization initiation source used. The reaction temperature is preferably 20° C. to 200° C., more preferably 30° C. to 140° C.

In the second step (polymerization step), the respective polymerizable monomers can be charged into the reactor at one time. Depending on the size of the reactor and the kinds of the monomers used, it may be preferable to charge a part or all of the monomers by sequential addition or continuous addition. Based on the knowledge of those skilled in the art, it is feasible to appropriately adjust the way of charging while observing the heat of reaction.

By the above-mentioned polymerization reaction, a solution or dispersion of the fluorine-containing polymer or copolymer is obtained. The organic solvent or water as the medium can be removed from the solution or dispersion by a known method such as fluorine-containing polymer or copolymer can be recovered by recrystallization, filtration, water washing, heating distillation under reduced pressure or the like. The thus-obtained fluorine-containing polymer or copolymer generally has a weight-average molecular weight of 1,000 to 100,000 and a molecular weight dispersion degree of 1 to 4.

EXAMPLES

The present invention will be described in more detail below by way of the following Examples. It should be understood that the following Examples are not intended to limit the present invention thereto.

In the following Examples, the purity of respective polymerizable monomers was measured by gas chromatography (GC); and polymerization impurities (such as oligomer and polymer) contained in the respective polymerizable monomers were measured by gel permeation chromatography (GPC). Further, the molecular weight and molecular weight dispersion degree of fluorine-containing polymers and copolymers respectively obtained from the polymerizable monomers by the second step were measured by gel permeation chromatography (GPC). The respective measurement conditions were as follows.

[GC conditions]

Apparatus: GC 2010 manufactured by Shimadzu Corporation

Column: capillary column (DB-1 manufactured by Agilent J & W Inc., film thickness: 0.25 μm, inner diameter: 0.25 mm, length: 30 m)

Temperature program: temperature rise at 10° C./min from 100° C. (3 minutes retention) to 250° C. (10 minutes retention)

Vaporizing chamber/detector temperature: vaporizing chamber temperature: 250° C., detector temperature: 250° C.

Detector: flame ionization detector (FID)

Carrier gas: helium

[GPC conditions]

Apparatus: HLC-8320GPC manufactured by Tosoh Corporation

Column for polymerizable monomer analysis: TSKgel series (serial connection of G2500HXL, G2000HXL, G1000HXL and G1000HXL) manufactured by Tosoh Corporation Column for polymer analysis: TSKgel series (serial connection of G2500HXL, G2000HXL, G1000HXL and G1000HXL) manufactured by Tosoh Corporation Temperature program: 40° C. (retention)

Flow rate: 1 mL/min

Detector: Refractive Index Detector (RI)

Eluent: tetrahydrofuran (THF)

In each of the following Examples, the purity of the polymerizable monomer is expressed in units of GC area % for the sake of convenience. On the other hand, the amount of each polymerization inhibitor compound contained is expressed in units of mass % on the basis of the previously examined correlation between the GC area % and mass % of the polymerization inhibitor.

In the following Examples, the “fluorine-containing polymerizable monomer” according to the present invention is sometimes referred to as “monomer” or “polymerizable monomer” (or sometimes referred to as e.g. “monomer a”, “polymerizable monomer d” etc.).

Example 1: Distillation Purification of Monomer a (Isomer Mixture)

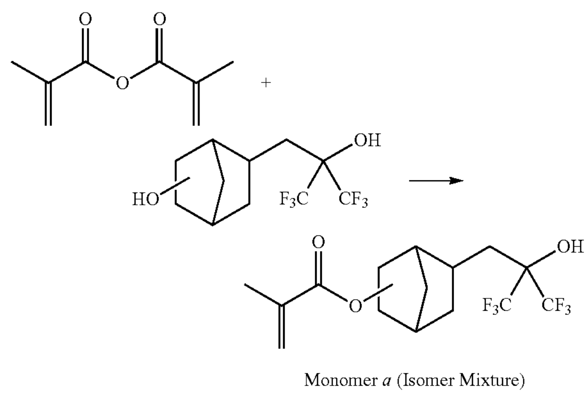

Monomer *a* (Isomer Mixture)

To a solution in which an alcohol (40 kg) shown in the above reaction scheme and methacrylic anhydride (with no polymerization inhibitor content; in a molar amount 0.95 times that of the alcohol) were dissolved in tetrahydrofuran (300 parts by mass per 100 parts by mass of the alcohol), 2,6-lutidine (in an molar amount 2 times that of the alcohol) was added. Further, 6-tert-butyl-2,4-xylenol (0.18 parts by mass per 100 parts by mass of the alcohol) and 2,2'-methylene-bis(4-methyl-6-tert-buthylphenol) (0.2 parts by mass per 100 parts by mass of the alcohol) were added as polymerization inhibitors to the solution. This solution was stirred for 8 hours at 50° C. under a nitrogen atmosphere. The resulting reaction solution was cooled to room temperature, followed by adding thereto water (in a mass amount 0.5 times that of the reaction solution) and stirring the reaction solution for 30 minutes at room temperature. After that, the reaction solution was left still for 30 minutes and separated into two layers. The organic layer (upper layer) was obtained by extracting the lower aqueous layer. The organic layer was further washed three times with water in the same manner as above. The organic layer was then subjected to flash distillation so as to distill out tetrahydrofuran and thereby obtain a crude product. The GC purity of the crude product (except for the remaining tetrahydrofuran solvent) was 90.5 area %. When the amounts of the respective polymerization initiators contained in the crude product were determined, the amount of 6-tert-butyl-2,4-xylenol contained was 0.10 mass %; and the amount of 2,2'-methylene-bis(4-methyl-6-tert-buthylphenol) contained was 0.13 mass %.

In a 20-L distillation apparatus (with a theoretical plate number of 4), 10 kg of the above-obtained crude product (unpurified polymerizable monomer a) was charged. To the crude product, 6-tert-butyl-2,4-xylenol as a polymerization inhibitor A (0.15 parts by mass per 100 parts by mass of the crude product) and 2,2'-methylene-bis(4-methyl-6-tert-buthylphenol) as a polymerization inhibitor B (0.12 parts by mass per 100 parts by mass of the crude product) were added. (As a result, the total amount of each of the polymerization inhibitors A and B was 0.25 parts by mass per 100 parts by mass of the crude product.)

The crude product was subsequently subjected to distillation under a reduced pressure of 0.1 to 0.3 kPa, while stirring, at an external temperature of 140 to 160° C. Herein, the distillation was performed for 5 hours at a reflux ratio of 1:1 while flowing 3% oxygen (nitrogen-diluted oxygen) at a speed of 0.5 L/min. After 0.8 kg of the initial fraction was separated, the distillate was switched to the main fraction. Then, 8.1 kg of the polymerizable monomer a (isomer mixture) was recovered as the main fraction. The GC purity of the polymerizable monomer a (isomer mixture) recovered as the main fraction (colorless transparent substance) was 97.0 area %. In GPC analysis of the main fraction, no peak was detected in oligomer/polymer region. The residue remaining after the distillation was confirmed to be high in flowability and was collected from a bottom discharge valve without clogging. The amount of the distillation residue collected was 0.9 kg. In GPC analysis of the distillation residue, no peak was detected in oligomer/polymer region. When the inside of the top portion of the distillation column was observed by a microscope, there were found no solid deposit and no polymer formation.

In Example 1, the distillation was performed using the same distillation raw material and distillation conditions as those in the after-mentioned Comparative Examples 1-1 and 1-2 except for the polymerization inhibitor. It was seen that, as compared with these Comparative Examples, polymerization of the distillation raw material in the distillation apparatus (the distillation residue, the top portion of the distillation column and the distillate) was significantly suppressed in Example 1. Further, it was seen that the occurrence of coloring during the distillation was suppressed in Example 1 as compared with the after-mentioned Comparative Example 1-3.

Comparative Example 1-1

To a solution in which an alcohol (40 kg) shown in the reaction scheme of Example 1 and methacrylic anhydride (with no polymerization inhibitor content; in a molar amount 0.95 times that of the alcohol) were dissolved in tetrahydrofuran (300 parts by mass per 100 parts by mass of the alcohol), 2,6-lutidine (in an molar amount 2 times that of the alcohol) was added. Further, 6-tert-butyl-2,4-xylenol (0.18 parts by mass per 100 parts by mass of the alcohol) as a polymerization inhibitor was added to the solution. This solution was stirred for 8 hours at 50° C. under a nitrogen atmosphere. The resulting reaction solution was cooled to room temperature, followed by adding thereto water (in a mass amount 0.5 times that of the reaction solution) and stirring the reaction solution for 30 minutes at room temperature. After that, the reaction solution was left still for 30 minutes and separated into two layers. The organic layer (upper layer) was obtained by extracting the lower aqueous layer. The organic layer was further washed three times with water in the same manner as above. The organic layer was then subjected to flash distillation so as to distill out tetrahydrofuran and thereby obtain a crude product. The GC purity of the crude product (except for the remaining tetrahydrofuran solvent) was 90.1 area %. The amount of 6-tert-butyl-2,4-xylenol contained as the polymerization initiator in the crude product was determined to be 0.10 mass %.

In a 20-L distillation apparatus (with a theoretical plate number of 4), 10 kg of the above-obtained crude product (unpurified polymerizable monomer a) was charged. To the crude product, 6-tert-butyl-2,4-xylenol as a polymerization inhibitor A (0.40 parts by mass per 100 parts by mass of the crude product) was added. (As a result, the total amount of the polymerization inhibitor A was 0.50 parts by mass per 100 parts by mass of the crude product.)

The crude product was subsequently subjected to distillation under a reduced pressure of 0.1 to 0.3 kPa, while stirring, at an external temperature of 140 to 160° C. Herein, the distillation was performed for 5 hours at a reflux ratio of 1:1 while flowing air at a speed of 0.5 L/min. After 0.8 kg of the initial fraction was separated, the distillate was switched to the main fraction. Then, 7.5 kg of the monomer a (isomer mixture) was recovered as the main fraction. The GC purity of the monomer a (isomer mixture) recovered as the main fraction (colorless transparent substance) was 96.7 area %. In GCP analysis of the main fraction, no peak was detected in oligomer/polymer region. In the residue remaining after the distillation, however, a viscosity increase was seen. It thus took time to collect the distillation residue from a bottom discharge valve. The amount of the distillation residue collected was 1.5 kg. In GPC analysis of the distillation residue, a peak of 32 area % was detected in oligomer/polymer region. When the inside of the top portion of the distillation column was observed by a microscope, there were found no solid deposit and no polymer formation.

Comparative Example 1-2

To a solution in which an alcohol (40 kg) shown in the reaction scheme of Example 1 and methacrylic anhydride (with no polymerization inhibitor content; in a molar amount 0.95 times that of the alcohol) were dissolved in tetrahydrofuran (300 parts by mass per 100 parts by mass of the alcohol), 2,6-lutidine (in an molar amount 2 times that of the alcohol) was added. Further, 2,2'-methylene-bis(4-methyl-6-tert-buthylphenol) (0.20 parts by mass per 100 parts by mass of the alcohol) as a polymerization inhibitor was added to the solution. This solution was stirred for 8 hours at 50° C. under a nitrogen atmosphere. The resulting reaction solution was cooled to room temperature, followed by adding thereto water (in a mass amount 0.5 times that of the reaction solution) and stirring the reaction solution for 30 minutes at room temperature. After that, the reaction solution was left still for 30 minutes and separated into two layers. The organic layer (upper layer) was obtained by extracting the lower aqueous layer. The organic layer was further washed three times with water in the same manner as above. The organic layer was then subjected to flash distillation so as to distill out tetrahydrofuran and thereby obtain a crude product. The GC purity of the crude product (except for the remaining tetrahydrofuran solvent) was 90.2 area %. The amount of 2,2'-methylene-bis(4-methyl-6-tert-buthylphenol) contained as the polymerization initiator in the crude product was determined to be 0.13 mass %.

In a 20-L distillation apparatus (with a theoretical plate number of 4), 10 kg of the above-obtained crude product (unpurified polymerizable monomer a) was charged. To the crude product, 2,2'-methylene-bis(4-methyl-6-tert-buthylphenol) as a polymerization inhibitor B (0.37 parts by mass per 100 parts by mass of the crude product) was added. (As a result, the total amount of the polymerization inhibitor B was 0.50 parts by mass per 100 parts by mass of the crude product.)

The crude product was subsequently subjected to distillation under a reduced pressure of 0.1 to 0.3 kPa, while stirring, at an external temperature of 140 to 160° C. Herein, the distillation was performed for 5 hours at a reflux ratio of 1:1 while flowing air at a speed of 0.5 L/min. After 0.8 kg of the initial fraction was separated, the distillate was switched to the main fraction. Then, 7.9 kg of the monomer a (isomer mixture) was recovered as the main fraction. The GC purity of the monomer a (isomer mixture) recovered as the main fraction (colorless transparent substance) was 96.9 area %. In GPC analysis of the main fraction, a peak of 0.5 area % was detected in oligomer/polymer region. The residue remaining after the distillation was confirmed to be high in flowability and was collected from a bottom discharge valve without clogging. The amount of the distillation residue collected was 1.1 kg. In GPC analysis of the distillation residue, no peak was detected in oligomer/polymer region. When the inside of the top portion of the distillation column was observed by a microscope, there were found no solid deposit and no polymer formation.

Comparative Example 1-3

To a solution in which an alcohol (40 kg) shown in the reaction scheme of Example 1 and methacrylic anhydride (with no polymerization inhibitor content; in a molar amount 0.95 times that of the alcohol) were dissolved in tetrahydrofuran (300 parts by mass per 100 parts by mass of the alcohol), 2,6-lutidine (in a molar amount 2 times that of the alcohol) was added. Further, phenothiazine (0.20 parts by mass per 100 parts by mass of the alcohol) as a polymerization inhibitor was added to the solution. This solution was stirred for 8 hours at 50° C. under a nitrogen atmosphere. The resulting reaction solution was cooled to room temperature, followed by adding thereto water (in a mass amount 0.5 times that of the reaction solution) and stirring the reaction solution for 30 minutes at room temperature. After that, the reaction solution was left still for 30 minutes and separated into two layers. The organic layer (upper layer) was obtained by extracting the lower aqueous layer. The organic layer was further washed three times with water in the same manner as above. The organic layer was then subjected to flash distillation so as to distill out tetrahydrofuran and thereby obtain a crude product. The GC purity of the crude product (except for the remaining tetrahydrofuran solvent) was 90.0 area %. The amount of phenothiazine contained as the polymerization initiator in the crude product was determined to be 0.15 mass %.

In a 20-L distillation apparatus (whose distillation column had a theoretical plate number of 4), 10 kg of the above-obtained crude product (unpurified polymerizable monomer a) was charged. To the crude product, phenothiazine as a polymerization inhibitor B (0.35 parts by mass per 100 parts by mass of the crude product) was added. (As a result, the total amount of phenothiazine was 0.50 parts by mass per 100 parts by mass of the crude product.)

The crude product was subsequently subjected to distillation under a reduced pressure of 0.1 to 0.3 kPa, while stirring, at an external temperature of 140 to 160° C. Herein, the distillation was performed for 5 hours at a reflux ratio of 1:1 while flowing air at a speed of 0.5 L/min. After 0.9 kg of the initial fraction was separated, the distillate was switched to the main fraction. Then, 7.3 kg of the monomer a (isomer mixture) was recovered as the main fraction. The GC purity of the monomer a (isomer mixture) recovered as the main fraction (pale pink substance) was 95.9 area %. In GPC analysis of the main fraction, no peak was detected in oligomer/polymer region. In the residue remaining after the distillation, however, a viscosity increase was seen. It thus took time to collect the distillation residue from a bottom discharge valve. The amount of the distillation residue collected was 1.6 kg. In GPC analysis of the distillation residue, a peak of 39 area % was detected in oligomer/polymer region. When the inside of the top portion of the distillation column was observed by a microscope, there were found no solid deposit and no polymer formation.

Example 2: Distillation Purification of Monomer b

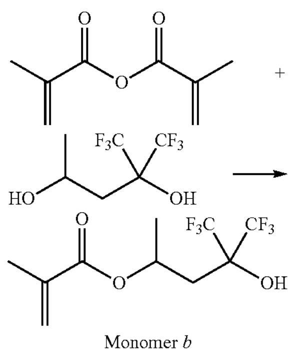

Monomer *b*

To a solution in which an alcohol (40 kg) shown in the above reaction scheme and methacrylic anhydride (with no polymerization inhibitor content; in a molar amount 1 time that of the alcohol) were dissolved in tetrahydrofuran (300 parts by mass per 100 parts by mass of the alcohol), 2,6-lutidine (in an molar amount 2 times that of the alcohol) was added. Further, 6-tert-butyl-2,4-xylenol (0.2 parts by mass per 100 parts by mass of the alcohol) and 2,2'-methylene-bis(4-methyl-6-tert-buthylphenol) (0.2 parts by mass per 100 parts by mass of the alcohol) were added as polymerization inhibitors to the solution. This solution was stirred for 5 hours at 40° C. under a nitrogen atmosphere. The resulting reaction solution was cooled to room temperature, followed by adding thereto water (in a mass amount 0.5 times that of the reaction solution) and stirring the reaction solution for 30 minutes at room temperature. After that, the reaction solution was left still for 30 minutes and separated into two layers. The organic layer (upper layer) was obtained by extracting the lower aqueous layer. The organic layer was further washed three times with water in the same manner as above. The organic layer was then subjected to flash distillation so as to distill out tetrahydrofuran and thereby obtain a crude product. The GC purity of the crude product (except for the remaining tetrahydrofuran solvent) was 96.5 area %. When the amounts of the respective polymerization initiators contained in the crude product were determined, the amount of 6-tert-butyl-2,4-xylenol was 0.10 mass %; and the amount of 2,2'-methylene-bis(4-methyl-6-tert-buthylphenol) was 0.15 mass %.

In a 30-L distillation apparatus with a theoretical plate number of 8; and with an irregular packing), 15 kg of the above-obtained crude product (unpurified polymerizable monomer b) was charged. To the crude product, 6-tert-butyl-2,4-xylenol as a polymerization inhibitor A (0.1 parts by mass per 100 parts by mass of the crude product) and 2,2'-methylene-bis(4-methyl-6-tert-buthylphenol) as a polymerization inhibitor B (0.05 parts by mass per 100 parts by mass of the crude product) were added. (As a result, the total amount of each of the polymerization inhibitors A and B was 0.20 parts by mass per 100 parts by mass of the crude product.)

The crude product was subsequently subjected to distillation under a reduced pressure of 1 to 3 kPa, while stirring, at an external temperature of 120 to 130° C. Herein, the distillation was performed for 8 hours at a reflux ratio of 1:5 while flowing 3% oxygen (nitrogen-diluted oxygen) at a speed of 0.5 L/min. After 1.1 kg of the initial fraction was separated, the distillate was switched to the main fraction. Then, 12.0 kg of the polymerizable monomer b was recovered as the main fraction. The GC purity of the polymerizable monomer b recovered as the main fraction (colorless transparent substance) was 99.6 area %. In GPC analysis of the main fraction, no peak was detected in oligomer/polymer region. The residue remaining after the distillation was confirmed to be high in flowability and was collected from a bottom discharge valve without clogging. The amount of the distillation residue collected was 1.7 kg. In GPC analysis of the distillation residue, no peak was detected in oligomer/polymer region. When the inside of the top portion of the distillation column was observed by a microscope, there were found no solid deposit and no polymer formation.

In Example 2, the distillation was performed using the same distillation raw material and distillation conditions as those in the after-mentioned Comparative Examples 2-1 and 2-2 except for the polymerization inhibitor. It was seen that, as compared with these Comparative Examples, polymerization of the distillation raw material in the distillation apparatus (the distillation residue, the top portion of the distillation column and the distillate) was significantly suppressed in Example 2.

Comparative Example 2-1

To a solution in which an alcohol (40 kg) shown in the reaction scheme of Example 2 and methacrylic anhydride (with no polymerization inhibitor content; in a molar amount 1 time that of the alcohol) were dissolved in tetrahydrofuran (300 parts by mass per 100 parts by mass of the alcohol), 2,6-lutidine (in an molar amount 2 times that of the alcohol) was added. Further, 6-tert-butyl-2,4-xylenol (0.2 parts by mass per 100 parts by mass of the alcohol) as a polymerization inhibitor was added to the solution. This solution was stirred for 5 hours at 40° C. under a nitrogen atmosphere. The resulting reaction solution was cooled to room temperature, followed by adding thereto water (in a mass amount 0.5 times that of the reaction solution) and stirring the reaction solution for 30 minutes at room temperature. After that, the reaction solution was left still for 30 minutes and separated into two layers. The organic layer (upper layer) was obtained by extracting the lower aqueous layer. The organic layer was further washed three times with water in the same manner as above. The organic layer was then subjected to flash distillation so as to distill out tetrahydrofuran and thereby obtain a crude product. The GC purity of the crude product (except for the remaining tetrahydrofuran solvent) was 96.3 area %. The amount of 6-tert-butyl-2,4-xylenol contained as the polymerization initiator in the crude product was determined to be 0.10 mass %.

In a 30-L distillation apparatus (with a theoretical plate number of 8; and with an irregular packing), 15 kg of the above-obtained crude product (unpurified polymerizable monomer b) was charged. To the crude product, 6-tert-butyl-2,4-xylenol as a polymerization inhibitor A (0.3 parts by mass per 100 parts by mass of the crude product) was added. (As a result, the total amount of the polymerization inhibitor A was 0.40 parts by mass per 100 parts by mass of the crude product.)

The crude product was subsequently subjected to distillation under a reduced pressure of 1 to 3 kPa, while stirring, at an external temperature of 120 to 130° C. Herein, the distillation was performed while flowing air at a speed of 0.5 L/min. After 1.2 kg of the initial fraction was separated, the distillate was switched to the main fraction. Then, 11.1 kg of the monomer b was recovered as the main fraction. The GC purity of the monomer b recovered as the main fraction (colorless transparent substance) was 99.4 area %. In GPC analysis of the main fraction, no peak was detected in oligomer/polymer region. In the residue remaining after the distillation, however, a viscosity increase was seen. It thus took time to collect the distillation residue from a bottom discharge valve. The amount of the distillation residue collected was 1.6 kg. In GPC analysis of the distillation residue, a peak of 8.2 area % was detected in oligomer/polymer region. When the inside of the top portion of the distillation column was observed by a microscope, there were found no solid deposit and no polymer formation.

Comparative Example 2-2

To a solution in which an alcohol (40 kg) shown in the reaction scheme of Example 2 and methacrylic anhydride (with no polymerization inhibitor content; in a molar amount 1 time that of the alcohol) were dissolved in tetrahydrofuran (300 parts by mass per 100 parts by mass of the alcohol), 2,6-lutidine (in an molar amount 2 times that of the alcohol) was added. Further, 2,2'-methylene-bis(4-methyl-6-tert-butylphenol) (0.20 parts by mass per 100 parts by mass of the alcohol) as a polymerization inhibitor was added to the solution. This solution was stirred for 5 hours at 40° C. under a nitrogen atmosphere. The resulting reaction solution was cooled to room temperature, followed by adding thereto water (in a mass amount 0.5 times that of the reaction solution) and stirring the reaction solution for 30 minutes at room temperature. After that, the reaction solution was left still for 30 minutes and separated into two layers. The organic layer (upper layer) was obtained by extracting the lower aqueous layer. The organic layer was further washed three times with water in the same manner as above. The organic layer was then subjected to flash distillation so as to distill out tetrahydrofuran and thereby obtain a crude product. The GC purity of the crude product (except for the remaining tetrahydrofuran solvent) was 96.4 area %. The amount of 2,2'-methylene-bis(4-methyl-6-tert-butylphenol) contained as the polymerization initiator in the crude product was determined to be 0.15 mass %.

In a 30-L distillation apparatus (with a theoretical plate number of 8; and with an irregular packing), 15 kg of the above-obtained crude product (unpurified monomer b) was charged. To the crude product, 2,2'-methylene-bis(4-methyl-6-tert-butylphenol) as a polymerization inhibitor B (0.25 parts by mass per 100 parts by mass of the crude product) was added. (As a result, the total amount of the polymerization inhibitor B was 0.40 parts by mass per 100 parts by mass of the crude product.)

The crude product was subsequently subjected to distillation under a reduced pressure of 1 to 3 kPa, while stirring, at an external temperature of 120 to 130° C. Herein, the distillation was performed for 8 hours at a reflux ratio of 1:5 while flowing 3% oxygen (nitrogen-diluted oxygen) at a speed of 0.5 L/min. After 1.1 kg of the initial fraction was separated, the distillate was switched to the main fraction. Then, 11.9 kg of the polymerizable monomer b was recovered as the main fraction. The GC purity of the polymerizable monomer b recovered as the main fraction (colorless transparent substance) was 99.0 area %. In GPC analysis of the main fraction, a peak of 0.8 area % was detected in oligomer/polymer region. The residue remaining after the distillation was confirmed to be high in flowability and was collected from a bottom discharge valve without clogging. The amount of the distillation residue collected was 1.8 kg. In GPC analysis of the distillation residue, no peak was detected in oligomer/polymer region. When the inside of the top portion of the distillation column was observed by a microscope, there was found a white solid deposit. It was impossible to completely remove the white solid deposit from the distillation column even by repeated cleaning with acetone under heating. Hence, the distillation apparatus was restored by disassembling the distillation column and physically scraping off the white solid deposit.

Example 3: Distillation Purification of Monomer c

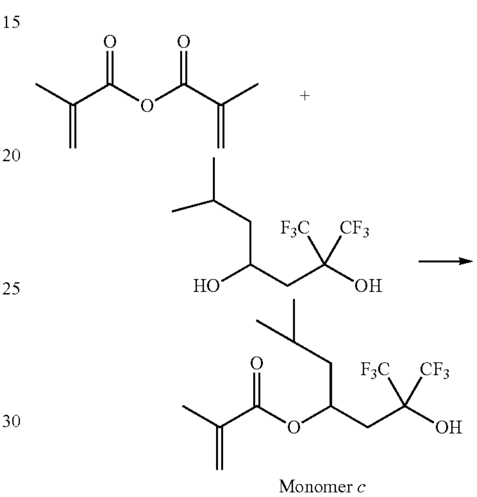

Monomer *c*

To a solution in which an alcohol (40 kg) shown in the above reaction scheme and methacrylic anhydride (with no polymerization inhibitor content; in a molar amount 1 time that of the alcohol) were dissolved in tetrahydrofuran (400 parts by mass per 100 parts by mass of the alcohol), triethylamine (in an molar amount 2 times that of the alcohol) was added. Further, 6-tert-butyl-2,4-xylenol (0.2 parts by mass per 100 parts by mass of the alcohol) and 2,2'-methylene-bis(4-ethyl-6-tert-buthylphenol) (0.2 parts by mass per 100 parts by mass of the alcohol) were added as polymerization inhibitors to the solution. This solution was stirred for 6 hours at 50° C. under a nitrogen atmosphere. The resulting reaction solution was cooled to room temperature, followed by adding thereto water (in a mass amount 0.5 times that of the reaction solution) and stirring the reaction solution for 30 minutes at room temperature. After that, the reaction solution was left still for 30 minutes and separated into two layers. The organic layer (upper layer) was obtained by extracting the lower aqueous layer. The organic layer was further washed two times with water in the same manner as above. The organic layer was then subjected to flash distillation so as to distill out tetrahydrofuran and thereby obtain a crude product. The GC purity of the crude product (except for the remaining tetrahydrofuran solvent) was 97.2 area %. When the amounts of the respective polymerization initiators contained in the crude product were determined, the amount of 6-tert-butyl-2,4-xylenol was 0.12 mass %; and the amount of 2,2'-methylene-bis(4-ethyl-6-tert-buthylphenol) was 0.15 mass %.

In a 30-L distillation apparatus (with a theoretical plate number of 8; and with an irregular packing), 12 kg of the above-obtained crude product (unpurified polymerizable monomer c) was charged. To the crude product, 6-tert-butyl- 2,4-xylenol as a polymerization inhibitor A (0.08 parts by mass per 100 parts by mass of the crude product) and 2,2'-methylene-bis(4-ethyl-6-tert-buthylphenol) as a polymerization inhibitor B (0.05 parts by mass per 100 parts by mass of the crude product) were added. (As a result, the total amount of each of the polymerization inhibitors A and B was 0.20 parts by mass per 100 parts by mass of the crude product.)

The crude product was subsequently subjected to distillation under a reduced pressure of 1 to 3 kPa, while stirring, at an external temperature of 125 to 140° C. Herein, the distillation was performed for 8 hours at a reflux ratio of 1:5 while flowing 3% oxygen (nitrogen-diluted oxygen) at a speed of 0.5 L/min. After 0.8 kg of the initial fraction was separated, the distillate was switched to the main fraction. Then, 9.5 kg of the polymerizable monomer c was recovered as the main fraction. The GC purity of the polymerizable monomer c recovered as the main fraction (colorless transparent substance) was 99.8 area %. In GPC analysis of the main fraction, no peak was detected in oligomer/polymer region. The residue remaining after the distillation was confirmed to be high in flowability and was collected from a bottom discharge valve without clogging. The amount of the distillation residue collected was 1.3 kg. In GPC analysis of the distillation residue, no peak was detected in oligomer/polymer region. When the inside of the top portion of the distillation column was observed by a microscope, there were found no solid deposit and no polymer formation.

In Example 3, the distillation was performed using the same distillation raw material and distillation conditions as those in the after-mentioned Comparative Examples 3-1 and 3-2 except for the polymerization inhibitor. It was seen that, as compared with these Comparative Examples, polymerization of the distillation raw material in the distillation apparatus (the distillation residue, the top portion of the distillation column and the distillate) was significantly suppressed in Example 3.

Comparative Example 3-1

To a solution in which an alcohol (40 kg) shown in the reaction scheme of Example 3 and methacrylic anhydride (with no polymerization inhibitor content; in a molar amount 1 time that of the alcohol) were dissolved in tetrahydrofuran (400 parts by mass per 100 parts by mass of the alcohol), triethylamine (in an molar amount 2 times that of the alcohol) was added. Further, 6-tert-butyl-2,4-xylenol (0.2 parts by mass per 100 parts by mass of the alcohol) as a polymerization inhibitor was added to the solution. This solution was stirred for 5 hours at 40° C. under a nitrogen atmosphere. The resulting reaction solution was cooled to room temperature, followed by adding thereto water (in a mass amount 0.5 times that of the reaction solution) and stirring the reaction solution for 30 minutes at room temperature. After that, the reaction solution was left still for 30 minutes and separated into two layers. The organic layer (upper layer) was obtained by extracting the lower aqueous layer. The organic layer was further washed two times with water in the same manner as above. The organic layer was then subjected to flash distillation so as to distill out tetrahydrofuran and thereby obtain a crude product. The GC purity of the crude product (except for the remaining tetrahydrofuran solvent) was 96.9 area %. When the amount of 6-tert-butyl-2,4-xylenol contained as the polymerization initiator in the crude product was determined to be 0.12 mass %.

In a 30-L distillation apparatus (with a theoretical plate number of 8; and with an irregular packing), 12 kg of the above-obtained crude product (unpurified polymerizable monomer c) was charged. To the crude product, 6-tert-butyl-2,4-xylenol as a polymerization inhibitor A (0.28 parts by mass per 100 parts by mass of the crude product) was added. (As a result, the total amount of the polymerization inhibitor A was 0.40 parts by mass per 100 parts by mass of the crude product.)

The crude product was subsequently subjected to distillation under a reduced pressure of 1 to 3 kPa, while stirring, at an external temperature of 125 to 140° C. Herein, the distillation was performed for 8 hours at a reflux ratio of 1:5 while flowing 3% oxygen (nitrogen-diluted oxygen) at a speed of 0.5 L/min. After 0.8 kg of the initial fraction was separated, the distillate was switched to the main fraction. Then, 9.3 kg of the polymerizable monomer c was recovered as the main fraction. The GC purity of the monomer c recovered as the main fraction (colorless transparent substance) was 99.5 area %. In GPC analysis of the main fraction, no peak was detected in oligomer/polymer region. The residue remaining after the distillation was confirmed to be high in flowability and was collected from a bottom discharge valve without clogging. In GPC analysis of the distillation residue, however, a peak of 2.2 area % was detected in oligomer/polymer region. The amount of the distillation residue collected was 1.5 kg. When the inside of the top portion of the distillation column was observed by a microscope, there were found no solid deposit and no polymer formation.

Comparative Example 3-2

To a solution in which an alcohol (40 kg) shown in the reaction scheme of Example 3 and methacrylic anhydride (with no polymerization inhibitor content; in a molar amount 1 time that of the alcohol) were dissolved in tetrahydrofuran (400 parts by mass per 100 parts by mass of the alcohol), triethylamine (in an molar amount 2 times that of the alcohol) was added. Further, 2,2'-methylene-bis(4-ethyl-6-tert-butylphenol) (0.20 parts by mass per 100 parts by mass of the alcohol) as a polymerization inhibitor was added to the solution. This solution was stirred for 5 hours at 40° C. under a nitrogen atmosphere. The resulting reaction solution was cooled to room temperature, followed by adding thereto water (in a mass amount 0.5 times that of the reaction solution) and stirring the reaction solution for 30 minutes at room temperature. After that, the reaction solution was left still for 30 minutes and separated into two layers. The organic layer (upper layer) was obtained by extracting the lower aqueous layer. The organic layer was further washed two times with water in the same manner as above. The organic layer was then subjected to flash distillation so as to distill out tetrahydrofuran and thereby obtain a crude product. The GC purity of the crude product (except for the remaining tetrahydrofuran solvent) was 97.1 area %. When the amount of 2,2'-methylene-bis(4-ethyl-6-tert-butylphenol) contained as the polymerization initiator in the crude product was determined to be 0.16 mass %.

In a 30-L distillation apparatus (with a theoretical plate number of 8; and with an irregular packing), 12 kg of the above-obtained crude product (unpurified polymerizable monomer c) was charged. To the crude product, 2,2'-methylene-bis(4-ethyl-6-tert-butylphenol) as a polymerization inhibitor B (0.24 parts by mass per 100 parts by mass of the crude product) was added. (As a result, the total amount of the polymerization inhibitor B was 0.40 parts by mass per 100 parts by mass of the crude product.)

The crude product was subsequently subjected to distillation under a reduced pressure of 1 to 3 kPa, while stirring, at an external temperature of 125 to 140° C. Herein, the distillation was performed for 8 hours at a reflux ratio of 1:5 while flowing 3% oxygen (nitrogen-diluted oxygen) at a speed of 0.5 L/min. After 0.8 kg of the initial fraction was separated, the distillate was switched to the main fraction. Then, 9.4 kg of the polymerizable monomer c was recovered as the main fraction. The GC purity of the monomer c recovered as the main fraction (colorless transparent substance) was 99.0 area %. In GPC analysis of the main fraction, a peak of 0.1 area % was detected in oligomer region. The residue remaining after the distillation was confirmed to be high in flowability and was collected from a bottom discharge valve without clogging. The amount of the distillation residue collected was 1.4 kg. In GPC analysis of the distillation residue, no peak was detected in oligomer/polymer region. When the inside of the top portion of the distillation column was observed by a microscope, there were found no solid deposit and no polymer formation.

Example 4: Distillation Purification of Monomer d

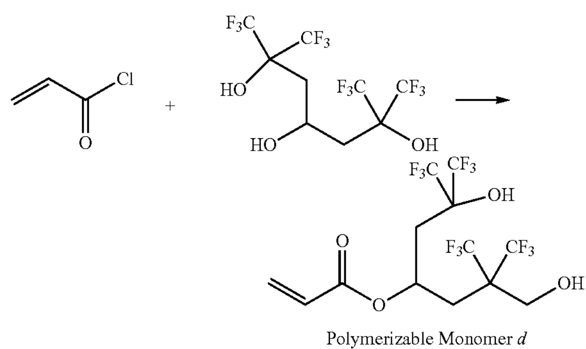

Polymerizable Monomer *d*

To a solution in which an alcohol (30 kg) shown in the above reaction scheme and acrylic acid chloride (in a molar amount 1.05 times that of the alcohol) were dissolved in tetrahydrofuran (400 parts by mass per 100 parts by mass of the alcohol), triethylamine (in an molar amount 2.1 times that of the alcohol) and N,N-dimethyl-4-aminopyridine (0.05 parts by mass per 100 parts by mass of the alcohol) were added. Further, methoquinone (0.2 parts by mass per 100 parts by mass of the alcohol) and 2,2'-methylene-bis(4-ethyl-6-tert-buthylphenol) (0.2 parts by mass per 100 parts by mass of the alcohol) were added as polymerization inhibitors to the solution. This solution was stirred for 5 hours at 40° C. under a nitrogen atmosphere. The resulting reaction solution was cooled to room temperature, followed by adding thereto water (in a mass amount 0.5 times that of the reaction solution) and stirring the reaction solution for 30 minutes at room temperature. After that, the reaction solution was left still for 30 minutes and separated into two layers. The organic layer (upper layer) was obtained by extracting the lower aqueous layer. The organic layer was further washed three times with water in the same manner as above. The organic layer was then subjected to flash distillation so as to distill out tetrahydrofuran and thereby obtain a crude product. The GC purity of the crude product (except for the remaining tetrahydrofuran solvent) was 95.8 area %. When the amounts of the respective polymerization initiators contained in the crude product were determined, the amount of methoquinone was 0.08 mass %; and the amount of 2,2'-methylene-bis(4-ethyl-6-tert-buthylphenol) was 0.1 mass %.

In a 20-L distillation apparatus (with a theoretical plate number of 4), 10 kg of the above-obtained crude product (unpurified polymerizable monomer d) was charged. To the crude product, methoquinone as a polymerization inhibitor A (0.12 parts by mass per 100 parts by mass of the crude product) and 2,2'-methylene-bis(4-ethyl-6-tert-buthylphenol) as a polymerization inhibitor B (0.1 parts by mass per 100 parts by mass of the crude product) were added. (As a result, the total amount of each of the polymerization inhibitors A and B was 0.20 parts by mass per 100 parts by mass of the crude product.)

The crude product was subsequently subjected to distillation under a reduced pressure of 0.5 to 2 kPa, while stirring, at an external temperature of 130 to 145° C. Herein, the distillation was performed for 5 hours at a reflux ratio of 1:1 while flowing 3% oxygen (nitrogen-diluted oxygen) at a speed of 0.5 L/min. After 0.9 kg of the initial fraction was separated, the distillate was switched to the main fraction. Then, 7.3 kg of the polymerizable monomer d was recovered as the main fraction. The GC purity of the polymerizable monomer d recovered as the main fraction (colorless transparent substance) was 98.5 area %. In GPC analysis of the main fraction, no peak was detected in oligomer/polymer region. The residue remaining after the distillation was confirmed to be high in flowability and was collected from a bottom discharge valve without clogging. In GPC analysis of the distillation residue, however, a peak of 2.2 area % was detected in oligomer/polymer region. The amount of the distillation residue collected was 1.5 kg. When the inside of the top portion of the distillation column was observed by a microscope, there were found no solid deposit and no polymer formation.

In Example 4, the distillation was performed using the same distillation raw material and distillation conditions as those in the after-mentioned Comparative Examples 4-1 and 4-2 except for the polymerization inhibitor. It was seen that, as compared with these Comparative Examples, polymerization of the distillation raw material in the distillation apparatus (the distillation residue, the top portion of the distillation column and the distillate) was significantly suppressed in Example 4.

Comparative Example 4-1

To a solution in which an alcohol (30 kg) shown in the reaction scheme of Example 4 and acrylic acid chloride (in a molar amount 1.05 times that of the alcohol) were dissolved in tetrahydrofuran (400 parts by mass per 100 parts by mass of the alcohol), triethylamine (in an molar amount 2.1 times that of the alcohol) and N,N-dimethyl-4-aminopyridine (0.05 parts by mass per 100 parts by mass of the alcohol) were added. Further, methoquinone (0.2 parts by mass per 100 parts by mass of the alcohol) as a polymerization inhibitor was added to the solution. This solution was stirred for 5 hours at 40° C. under a nitrogen atmosphere. The resulting reaction solution was cooled to room temperature, followed by adding thereto water (in a mass amount 0.5 times that of the reaction solution) and stirring the reaction solution for 30 minutes at room temperature. After that, the reaction solution was left still for 30 minutes and separated into two layers. The organic layer (upper layer) was obtained by extracting the lower aqueous layer. The organic layer was further washed three times with water in the same manner as above. The organic layer was then subjected to flash distillation so as to distill out tetrahydrofuran and thereby obtain a crude product. The GC purity of the crude product (except for the remaining tetrahydrofuran solvent) was 95.8 area %. The amount of methoquinone contained as the polymerization inhibitor in the crude product was determined to be 0.08 mass %.

In a 20-L distillation apparatus (with a theoretical plate number of 4), 10 kg of the above-obtained crude product (unpurified polymerizable monomer d) was charged. To the crude product, methoquinone as a polymerization inhibitor A (0.32 parts by mass per 100 parts by mass of the crude product) was added. (As a result, the total amount of the polymerization inhibitor A was 0.40 parts by mass per 100 parts by mass of the crude product.)

The crude product was subsequently subjected to distillation under a reduced pressure of 0.5 to 2 kPa, while stirring, at an external temperature of 130 to 145° C. Herein, the distillation was performed for 5 hours at a reflux ratio of 1:1 while flowing 3% oxygen (nitrogen-diluted oxygen) at a speed of 0.5 L/min. After 0.9 kg of the initial fraction was separated, the distillate was switched to the main fraction. Then, 7.0 kg of the polymerizable monomer d was recovered as the main fraction. The GC purity of the polymerizable monomer d recovered as the main fraction (colorless transparent substance) was 98.8 area %. In GPC analysis of the main fraction, no peak was detected in oligomer/polymer region. In the residue remaining after the distillation, however, a viscosity increase was seen. It thus took time to collect the distillation residue from a bottom discharge valve. The amount of the distillation residue collected was 1.0 kg. In GPC analysis of the distillation residue, a peak of 44 area % was detected in oligomer/polymer region. When the inside of the top portion of the distillation column was observed by a microscope, there were found no solid deposit and no polymer formation.

Comparative Example 4-2

To a solution in which an alcohol (30 kg) shown in the reaction scheme of Example 4 and acrylic acid chloride (in a molar amount 1.05 times that of the alcohol) were dissolved in tetrahydrofuran (400 parts by mass per 100 parts by mass of the alcohol), triethylamine (in an molar amount 2.1 times that of the alcohol) and N,N-dimethyl-4-aminopyridine (0.05 parts by mass per 100 parts by mass of the alcohol) were added. Further, 2,2'-methylene-bis(4-ethyl-6-tert-butylphenol) (0.2 parts by mass per 100 parts by mass of the alcohol) as a polymerization inhibitor was added to the solution. This solution was stirred for 5 hours at 40° C. under a nitrogen atmosphere. The resulting reaction solution was cooled to room temperature, followed by adding thereto water (in a mass amount 0.5 times that of the reaction solution) and stirring the reaction solution for 30 minutes at room temperature. After that, the reaction solution was left still for 30 minutes and separated into two layers. The organic layer (upper layer) was obtained by extracting the lower aqueous layer. The organic layer was further washed three times with water in the same manner as above. The organic layer was then subjected to flash distillation so as to distill out tetrahydrofuran and thereby obtain a crude product. The GC purity of the crude product (except for the remaining tetrahydrofuran solvent) was 95.8 area %. The amount of 2,2'-methylene-bis(4-ethyl-6-tert-butylphenol) contained as the polymerization inhibitor in the crude product was determined to be 0.1 mass %.

In a 20-L distillation apparatus (with a theoretical plate number of 4), 10 kg of the above-obtained crude product (unpurified polymerizable monomer d) was charged. To the crude product, 2,2'-methylene-bis(4-ethyl-6-tert-butylphenol) as a polymerization inhibitor B (0.3 parts by mass per 100 parts by mass of the crude product) was added. (As a result, the total amount of the polymerization inhibitor B was 0.40 parts by mass per 100 parts by mass of the crude product.)

The crude product was subsequently subjected to distillation under a reduced pressure of 0.5 to 2 kPa, while stirring, at an external temperature of 130 to 145° C. Herein, the distillation was performed for 5 hours at a reflux ratio of 1:1 while flowing 3% oxygen (nitrogen-diluted oxygen) at a speed of 0.5 L/min. After 0.8 kg of the initial fraction was separated, the distillate was switched to the main fraction. However, a flowability deterioration of the fraction was found from the middle of the distillation. Hence, the distillation was stopped. The GC purity of the polymerizable monomer d recovered as the main fraction (5.3 kg) was 96.2 area %. In GPC analysis of the main fraction, a peak of 5.9 area % was detected in oligomer/polymer region. The residue remaining after the distillation was confirmed to be high in flowability and was collected from a bottom discharge valve without clogging. The amount of the distillation residue collected was 2.9 kg. In GPC analysis of the distillation residue, a peak of 2.1 area % was detected in oligomer/polymer region. When the inside of the top portion of the distillation column was observed by a microscope, there was found a white solid deposit. It was impossible to completely remove the white solid deposit from the distillation column even by repeated cleaning with acetone under heating. Thus, the distillation apparatus was restored by disassembling the distillation column and physically scraping off the white solid deposit.

Example 5-1: Production of Fluorine-Containing Polymer (Homopolymer)

Using the polymerizable monomer a obtained in Example 1, a fluorine-containing polymer with a repeating unit (5a) was produced.

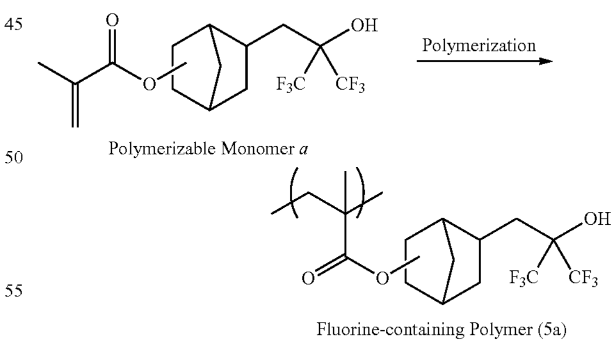

The production of the fluorine-containing polymer with the repeating unit (5a) will be specifically explained below.

In a 500-mL egg-plant shaped flask, the polymerizable monomer a (100 g) was charged at room temperature (about 20° C.) and admixed with 2-butanone (200 g) to form a uniform solution. Into this solution, dimethyl-2,2'-azobis(2-methylpropionate) (2.56 g) was added as a polymerization imitator and dissolved. The resulting solution was entirely transferred into a 500-mL dropping funnel. Next, 2-butanone (100 g) was charged in a 1-L four-neck flask equipped with a stirring blade, a Dimroth condenser and a thermometer, and then, refluxed under a nitrogen flow while heating with an oil bath. The above-prepared dropping funnel was attached to the four-neck flask. The butanone solution of the polymerization monomer a and the polymerization initiator was then dropped into the flask, with stirring, over 2 hours under a nitrogen flow while maintaining the reflux conditions. After the dropping, the solution in the flask was further stirred for 6 hours under a nitrogen flow while maintaining the reflux conditions. By removal of the oil bath, the flask was naturally cooled, with stirring, to an internal temperature of 30° C. under a nitrogen flow. The thus-obtained polymerization solution was entirely transferred into a 500-mL dropping funnel. Further, n-heptane (1600 g) was charged in a 3-L four-neck flask. The flask was controlled to an internal temperature of 25 to 30° C. with a water bath. In this state, the polymerization solution was dropped into the flask, with stirring, through the dropping funnel over 1 hour. While maintaining the internal temperature of the flask at 25 to 30° C., the polymerization solution was further stirred for 2 hours. Consequently, the solution of the fluorine-containing polymer (5a) was obtained in slurry solution form. The slurry solution was subjected to suction filtration with a filter paper (No. 5A manufactured by Advantec Corporation), thereby recovering the fluorine-containing polymer (5a). Then, the fluorine-containing polymer (5a) was admixed with and dissolved in 2-butanone (200 g) at room temperature. The butanone solution of the fluorine-containing polymer (5a) was entirely transferred into a 500-mL dropping funnel. After n-heptane (1600 g) was charged in a 3-L four-neck flask, the butanone solution of the fluorine-containing polymer (5a) was dropped into the flask, with stirring, through the dropping funnel over 1 hour while maintaining the flask at an internal temperature of 25 to 30° C. with a water bath. While maintaining the internal temperature of the flask at 25 to 30° C., the solution in the flask was further stirred for 2 hours. The solution of the fluorine-containing polymer (5a) was consequently obtained in slurry solution form. The slurry solution was subjected to suction filtration with a filter paper (No. 5A manufactured by Advantec Corporation), thereby recovering the fluorine-containing polymer (5a). The fluorine-containing polymer (5a) was dried in a shelf-type vacuum dryer (60° C. and 1 kPa) to remove the solvent therefrom. As a result, the polymer was obtained as a white powder (76 g). It was confirmed by GPC analysis that the weight-average molecular weight of the polymer was 11332; and the molecular weight dispersion degree of the polymer was 2.0.

Example 5-2: Production of Fluorine-containing Polymer (Homopolymer)

Using the polymerizable monomer b obtained in Example 2, a fluorine-containing polymer with a repeating unit (5b) was produced.

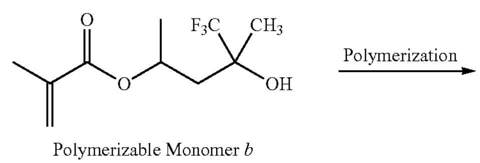

Polymerizable Monomer *b*

-continued

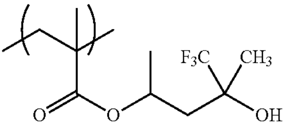

Fluorine-containing Polymer (5b)

The production of the fluorine-containing polymer with the repeating unit (5a) will be specifically explained below.

In a 500-mL egg-plant shaped flask, the polymerizable monomer b (100 g) was charged at room temperature (about 20° C.) and admixed with 2-propanol (200 g) to form a uniform solution. Into this solution, dimethyl-2,2'-azobis(2-methylpropionate) (6.26 g) was added as a polymerization imitator and dissolved. The resulting solution was entirely transferred into a 500-mL dropping funnel. Next, 2-propanol (100 g) was charged in a 1-L four-neck flask equipped with a stirring blade, a Dimroth condenser and a thermometer, and then, refluxed under a nitrogen flow while heating with an oil bath. The above-prepared dropping funnel was attached to the four-neck flask. The 2-propanol solution of the polymerization monomer b and the polymerization initiator was then dropped into the flask, with stirring, over 2 hours under a nitrogen flow while maintaining the reflux conditions. After the dropping, the solution in the flask was further stirred for 6 hours under a nitrogen flow while maintaining the reflux conditions. By removal of the oil bath, the flask was naturally cooled, with stirring, to an internal temperature of 30° C. under a nitrogen flow. The thus-obtained polymerization solution was entirely transferred into a 500-mL dropping funnel. Further, n-decane (1600 g) was charged in a 3-L four-neck flask. The flask was controlled to an internal temperature of 20 to 25° C. with a water bath. In this state, the polymerization solution was dropped into the flask, with stirring, through the dropping funnel over 1 hour. While maintaining the internal temperature of the flask at 20 to 25° C., the polymerization solution was further stirred for 2 hours. Consequently, the solution of the fluorine-containing polymer (5b) was obtained in slurry solution form. The slurry solution was subjected to suction filtration with a filter paper (No. 5A manufactured by Advantec Corporation), thereby recovering the fluorine-containing polymer (5b). Then, the fluorine-containing polymer (5b) was admixed with and dissolved in 2-propanol (200 g) at room temperature. The 2-propanol solution of the fluorine-containing polymer (5b) was entirely transferred into a 500-mL dropping funnel. After n-decane (1600 g) was charged in a 3-L four-neck flask, the 2-propanol solution of the fluorine-containing polymer (5b) was dropped into the flask, with stirring, through the dropping funnel over 1 hour while maintaining the flask at an internal temperature of 20 to 25° C. with a water bath. While maintaining the internal temperature of the flask at 20 to 25° C., the solution in the flask was further stirred for 2 hours. The solution of the fluorine-containing polymer (5b) was consequently obtained in slurry solution form. The slurry solution was subjected to suction filtration with a filter paper (No. 5A manufactured by Advantec Corporation), thereby recovering the fluorine-containing polymer (5b). The fluorine-containing polymer (5b) was dried in a shelf-type vacuum dryer (70° C. and 1 kPa) to remove the solvent therefrom. As a result, the polymer was obtained as a white powder (71 g). It was confirmed by GPC analysis that the weight-average molecular weight of the polymer was 12015; and the molecular weight dispersion degree of the polymer was 1.9.

Example 6-1: Production of Fluorine-Containing Copolymer (6a)

Using the polymerizable monomer a obtained in Example 1, a fluorine-containing polymer with a repeating unit (6a) was produced.

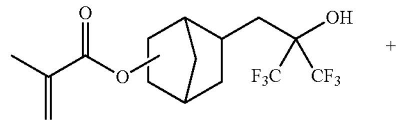

Polymerizable Monomer *a*

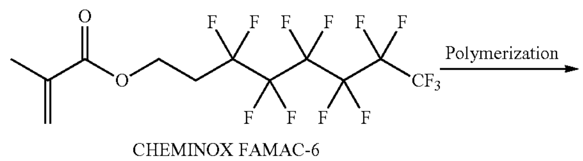

CHEMINOX FAMAC-6

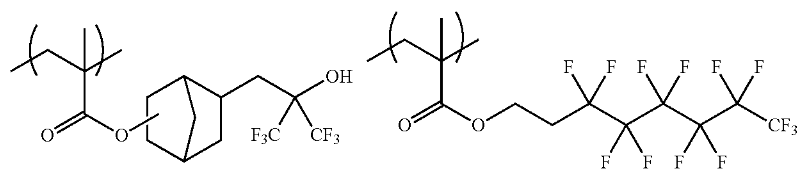

Fluorine-containing Polymer (6a)

The production of the fluorine-containing polymer with the repeating unit (6a) will be specifically explained below.

In a 500-mL egg-plant shaped flask, the polymerizable monomer a (45 g) obtained as the distillation fraction in Example 1 and 2-(perfluorohexyl)ethyl methacrylate (55 g) (manufactured under the product name of CHEMINOX FAMAC-6 by Unimatec Corporation) were charged at room temperature (about 20° C.). Subsequently, Novec 7300 (100 g) manufactured by 3M Corporation was added to these monomer compounds to thereby form a uniform solution. Into this solution, 2,2'-azobis(isobutyronitrile) (1.7 g) was added as a polymerization imitator and dissolved. The resulting solution was entirely transferred into a 500-mL dropping funnel. Next, Novec 7300 (200 g) was charged in a 1-L four-neck flask equipped with a stirring blade, a Dimroth condenser and a thermometer, and then, refluxed under a nitrogen flow while heating with an oil bath. The above-prepared dropping funnel was attached to the four-neck flask. The solution of the polymerization monomer a, CHEMINOX FAMAC-6 and the polymerization initiator in Novec 7300 was then dropped into the flask, with stirring, over 2 hours under a nitrogen flow while maintaining the reflux conditions. After the dropping, the solution in the flask was further stirred for 8 hours under a nitrogen flow while maintaining the reflux conditions. By removal of the oil bath, the flask was naturally cooled, with stirring, to an internal temperature of 30° C. under a nitrogen flow. The thus-obtained polymerization solution was entirely transferred into a 500-mL dropping funnel. Further, n-decane (1600 g) was charged in a 3-L four-neck flask. The flask was controlled to an internal temperature of 20 to 25° C. with a water bath. In this state, the polymerization solution was dropped into the flask, with stirring, through the dropping funnel over 1 hour. While maintaining the internal temperature of the flask at 20 to 25° C., the polymerization solution was further stirred for 2 hours. Consequently, the solution of the fluorine-containing polymer (6a) was obtained in slurry solution form. The slurry solution was subjected to suction filtration with a filter paper (No. 5A manufactured by Advantec Corporation), thereby recovering the fluorine-containing polymer (6a). Then, the fluorine-containing polymer (6a) was admixed with and dissolved in Novec 7300 (160 g) at room temperature. The solution of the fluorine-containing polymer (6a) in Novec 7300 was entirely transferred into a 500-mL dropping funnel. After n-decane (1600 g) was charged in a 3-L four-neck flask, the solution of the fluorine-containing polymer (6a) in Novec 7300 was dropped into the flask, with stirring, through the dropping funnel over 1 hour while maintaining the flask at an internal temperature of 20 to 25° C. with a water bath. While maintaining the internal temperature of the flask at 20 to 25° C., the solution in the flask was further stirred for 2 hours. The solution of the fluorine-containing polymer (6a) was consequently obtained in slurry solution form. The slurry solution was subjected to suction filtration with a filter paper (No. 5A manufactured by Advantec Corporation), thereby recovering the fluorine-containing polymer (6a). The fluorine-containing polymer (6a) was dried in a shelf-type vacuum dryer (60° C. and 1 kPa) to remove the solvent therefrom. As a result, the polymer was obtained as a white powder (90 g). It was confirmed by GPC analysis that the weight-average molecular weight of the polymer was 14230; and the molecular weight dispersion degree of the polymer was 2.0.

Example 6-2: Production of Fluorine-Containing Copolymer (6b)

Using the polymerizable monomer b obtained in Example 2, a fluorine-containing polymer with a repeating unit (6b) was produced.

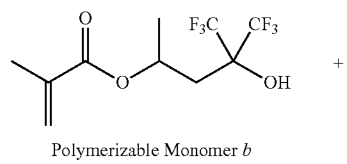

Polymerizable Monomer *b*

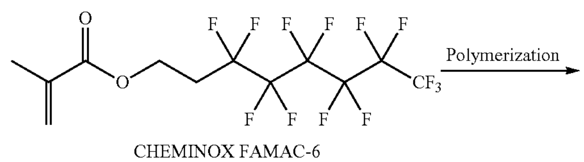

CHEMINOX FAMAC-6

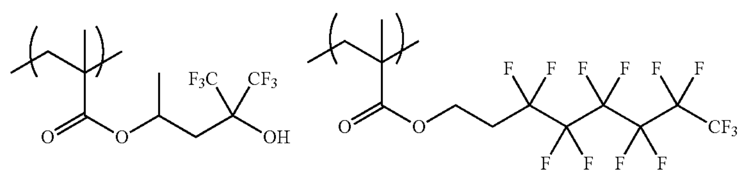

Fluorine-containing Polymer (6b)

The production of the fluorine-containing polymer with the repeating unit (6b) will be specifically explained below.

In a 500-mL egg-plant shaped flask, the polymerizable monomer b (64 g) obtained as the distillation fraction in Example 2 and 2-(perfluorohexyl)ethyl methacrylate (55 g) (manufactured under the product name of CHEMINOX FAMAC-6 by Unimatec Corporation) were charged at room temperature (about 20° C.). Subsequently, Novec 7300 (100 g) manufactured by 3M Corporation was added to these monomer compounds to thereby form a uniform solution. Into this solution, 2,2'-azobis(isobutyronitrile) (3.0 g) was added as a polymerization imitator and dissolved. The resulting solution was entirely transferred into a 500-mL dropping funnel. Next, Novec 7300 (200 g) was charged in a 1-L four-neck flask equipped with a stirring blade, a Dimroth condenser and a thermometer, and then, refluxed under a nitrogen flow while heating with an oil bath. The above-prepared dropping funnel was attached to the four-neck flask. The solution of the polymerization monomer b, CHEMINOX FAMAC-6 and the polymerization initiator in Novec 7300 was then dropped into the flask, with stirring, over 2 hours under a nitrogen flow while maintaining the reflux conditions. After the dropping, the solution in the flask was further stirred for 8 hours under a nitrogen flow while maintaining the reflux conditions. By removal of the oil bath, the flask was naturally cooled, with stirring, to an internal temperature of 30° C. under a nitrogen flow. The thus-obtained polymerization solution was entirely transferred into a 500-mL dropping funnel. Further, n-decane (1600 g) was charged in a 3-L four-neck flask. The flask was controlled to an internal temperature of 20 to 25° C. with a water bath. In this state, the polymerization solution was dropped into the flask, with stirring, through the dropping funnel over 1 hour. While maintaining the internal temperature of the flask at 20 to 25° C., the polymerization solution was further stirred for 2 hours. Consequently, the solution of the fluorine-containing polymer (6b) was obtained in slurry solution form. The slurry solution was subjected to suction filtration with a filter paper (No. 5A manufactured by Advantec Corporation), thereby recovering the fluorine-containing polymer (6b). Then, the fluorine-containing polymer (6b) was admixed with and dissolved in Novec 7300 (160 g) at room temperature. The solution of the fluorine-containing polymer (6b) in Novec 7300 was entirely transferred into a 500-mL dropping funnel. After n-decane (1600 g) was charged in a 3-L four-neck flask, the solution of the fluorine-containing polymer (6b) in Novec 7300 was dropped into the flask, with stirring, through the dropping funnel over 1 hour while maintaining the flask at an internal temperature of 20 to 25° C. with a water bath. While maintaining the internal temperature of the flask at 20 to 25° C., the solution in the flask was further stirred for 2 hours. The solution of the fluorine-containing polymer (6b) was consequently obtained in slurry solution form. The slurry solution was subjected to suction filtration with a filter paper (No. 5A manufactured by Advantec Corporation), thereby recovering the fluorine-containing polymer (6b). The fluorine-containing polymer (6b) was dried in a shelf-type vacuum dryer (60° C. and 1 kPa) to remove the solvent therefrom. As a result, the polymer was obtained as a white powder (86 g). It was confirmed by GPC analysis that the weight-average molecular weight of the polymer was 12110; and the molecular weight dispersion degree of the polymer was 1.9.

Example 6-3: Production of Fluorine-Containing Copolymer

Using the polymerizable monomer c obtained in Example 3, a fluorine-containing polymer with a repeating unit (6c) was produced.

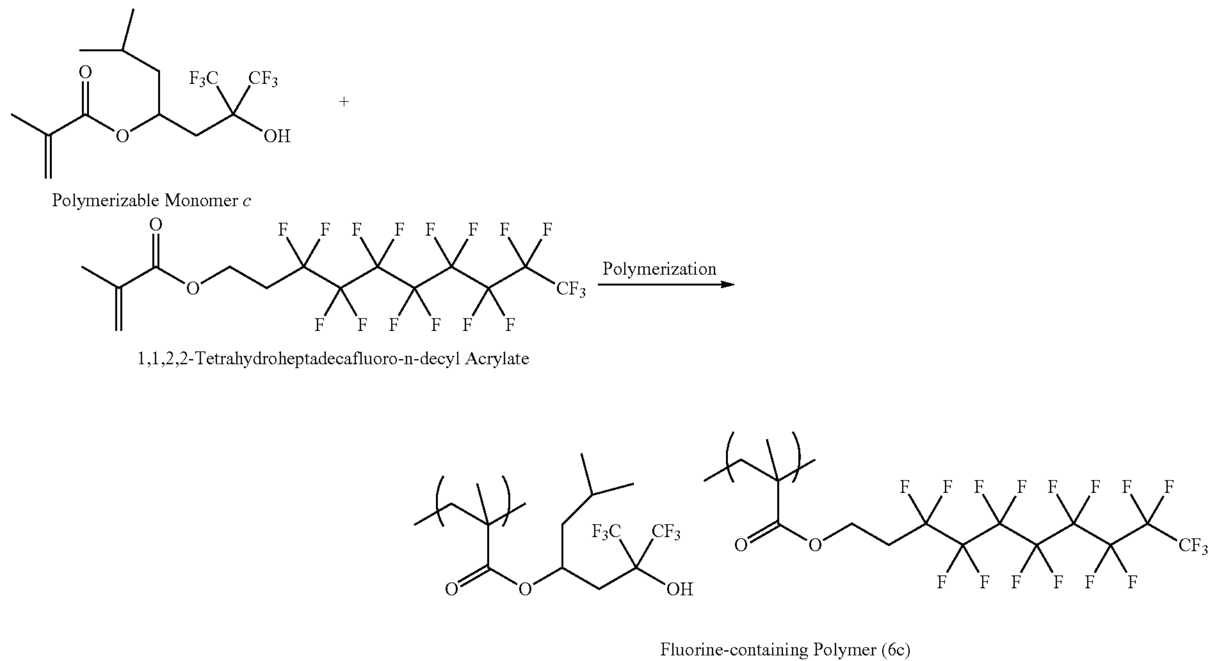

The production of the fluorine-containing polymer with the repeating unit (6c) will be specifically explained below.

In a 500-mL egg-plant shaped flask, the polymerizable monomer c (101 g) and 1,1,2,2-tetrahydroheptadecafluoro-n-decyl acrylate (18 g) were charged at room temperature (about 20° C.) and admixed with 2-butanone (238 g) to form a uniform solution. Into this solution, 2,2'-azobis(isobutyronitrile) (3.3 g) was added as a polymerization imitator and dissolved. The resulting solution was entirely transferred into a 500-mL dropping funnel. Next, 2-butanone (119 g) was charged in a 1-L four-neck flask equipped with a stirring blade, a Dimroth condenser and a thermometer, and then, refluxed under a nitrogen flow while heating with an oil bath. The above-prepared dropping funnel was attached to the four-neck flask. The 2-butanone solution of the polymerization monomer c, 1,1,2,2-tetrahydroheptadecafluoro-n-decyl acrylate and the polymerization initiator was then dropped into the flask, with stirring, over 2 hours under a nitrogen flow while maintaining the reflux conditions. After the dropping, the solution in the flask was further stirred for 6 hours under a nitrogen flow while maintaining the reflux conditions. By removal of the oil bath, the flask was naturally cooled, with stirring, to an internal temperature of 30° C. under a nitrogen flow. The thus-obtained polymerization solution was entirely transferred into a 500-mL dropping funnel. Further, n-decane (2142 g) was charged in a 3-L four-neck flask. The flask was controlled to an internal temperature of 15 to 20° C. with a water bath. In this state, the polymerization solution was dropped into the flask, with stirring, through the dropping funnel over 1 hour. While maintaining the internal temperature of the flask at 15 to 20° C., the polymerization solution was further stirred for 2 hours. Consequently, the solution of the fluorine-containing polymer (6c) was obtained in slurry solution form. The slurry solution was subjected to suction filtration with a filter paper (No. 5A manufactured by Advantec Corporation), thereby recovering the fluorine-containing polymer (6c). Then, the fluorine-containing polymer (6c) was admixed with and dissolved in 2-butanone (239 g) at room temperature. The 2-butanone solution of the fluorine-containing polymer (6c) was entirely transferred into a 500-mL dropping funnel. After n-decane (2142 g) was charged in a 3-L four-neck flask, the 2-butanone solution of the fluorine-containing polymer (6c) was dropped into the flask, with stirring, through the dropping funnel over 1 hour while maintaining the flask at an internal temperature of 15 to 20° C. with a water bath. While maintaining the internal temperature of the flask at 15 to 20° C., the solution in the flask was further stirred for 2 hours. The solution of the fluorine-containing polymer (6c) was consequently obtained in slurry solution form. The slurry solution was subjected to suction filtration with a filter paper (No. 5A manufactured by Advantec Corporation), thereby recovering the fluorine-containing polymer (6c). The fluorine-containing polymer (6c) was dried in a shelf-type vacuum dryer (60° C. and 1 kPa) to remove the solvent therefrom. As a result, the polymer was obtained as a white powder (66 g). It was confirmed by GPC analysis that the weight-average molecular weight of the polymer was 9029; and the molecular weight dispersion degree of the polymer was 1.9.

Example 6-4: Production of Fluorine-Containing Copolymer

Using the polymerizable monomer d obtained in Example 4, a fluorine-containing polymer with a repeating unit (6d) was produced.

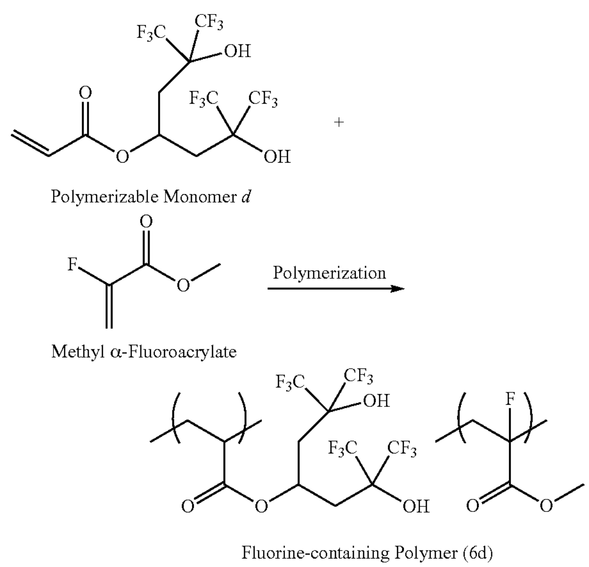

Fluorine-containing Polymer (6d)

The production of the fluorine-containing polymer with the repeating unit (6b) will be specifically explained below.

In a 500-mL egg-plant shaped flask, the polymerizable monomer d (85 g) and methyl α-fluoroacrylate (13 g) were charged at room temperature (about 20° C.) and admixed with n-butyl acetate (196 g) to form a uniform solution. Into this solution, 2,2'-azobis(isobutyronitrile) (4.2 g) was added as a polymerization imitator and dissolved. The resulting solution was entirely transferred into a 500-mL dropping funnel. Next, n-butyl acetate (98 g) was charged in a 1-L four-neck flask equipped with a stirring blade, a Dimroth condenser and a thermometer, and then, refluxed under a nitrogen flow while heating with an oil bath. The above-prepared dropping funnel was attached to the four-neck flask. The n-butyl acetate solution of the polymerization monomer d, methyl α-fluoroacrylate and the polymerization initiator was then dropped into the flask, with stirring, over 2 hours under a nitrogen flow while maintaining the reflux conditions. After the dropping, the solution in the flask was further stirred for 6 hours under a nitrogen flow while maintaining the reflux conditions. By removal of the oil bath, the flask was naturally cooled, with stirring, to an internal temperature of 30° C. under a nitrogen flow. The thus-obtained polymerization solution was entirely transferred into a 500-mL dropping funnel. Further, n-decane (1960 g) was charged in a 3-L four-neck flask. The flask was controlled to an internal temperature of 20 to 25° C. with a water bath. In this state, the polymerization solution was dropped into the flask, with stirring, through the dropping funnel over 1 hour. While maintaining the internal temperature of the flask at 20 to 25° C., the polymerization solution was further stirred for 2 hours. Consequently, the solution of the fluorine-containing polymer (6d) was obtained in slurry solution form. The slurry solution was subjected to suction filtration with a filter paper (No. 5A manufactured by Advantec Corporation), thereby recovering the fluorine-containing polymer (6d). Then, the fluorine-containing polymer (6d) was admixed with and dissolved in n-butyl acetate (196 g) at room temperature. The n-butyl acetate solution of the fluorine-containing polymer (6d) was entirely transferred into a 500-mL dropping funnel. After n-decane (1960 g) was charged in a 3-L four-neck flask, the n-butyl acetate solution of the fluorine-containing polymer (6d) was dropped into the flask, with stirring, through the dropping funnel over 1 hour while maintaining the flask at an internal temperature of 20 to 25° C. with a water bath. While maintaining the internal temperature of the flask at 20 to 25° C., the solution in the flask was further stirred for 2 hours. The solution of the fluorine-containing polymer (6d) was consequently obtained in slurry solution form. The slurry solution was subjected to suction filtration with a filter paper (No. 5A manufactured by Advantec Corporation), thereby recovering the fluorine-containing polymer (6d). The fluorine-containing polymer (6d) was dried in a shelf-type vacuum dryer (60° C. and 1 kPa) to remove the solvent therefrom. As a result, the polymer was obtained as a white powder (75 g). It was confirmed by GPC analysis that the weight-average molecular weight of the polymer was 10095; and the molecular weight dispersion degree of the polymer was 2.2.

As explained above, it was seen that the polymerizable monomer of the formula (1) purified by any of the methods of Examples 1 to 4 was smoothly converted to the polymer (homopolymer or heteropolymer) in the presence of the polymerization initiator. There was no hindrance caused to the reactivity of the polymerization by the combined use of the phenolic compound A and the phenolic compound B during the distillation.

The invention claimed is:

1. A purification method for purifying a fluorine-containing polymerizable monomer of the following general formula (1), comprising the following first step:

a distillation purification step of distilling the fluorine-containing polymerizable monomer in the presence of a phenolic compound A of the following formula (2) and a phenolic compound B of the following formula (3), thereby obtaining the fluorine-containing polymerizable monomer as a distillation fraction (1)

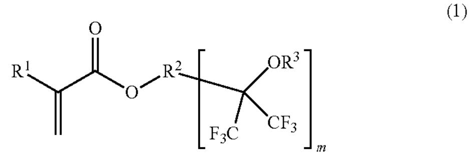

where $R^1$ is a group selected from a hydrogen atom, a halogen atom, a hydrocarbon group and a fluorine-containing alkyl group which is in straight or branched chain form and optionally contains a cyclic structure; $R^2$ is a divalent or trivalent organic group selected from an aliphatic hydrocarbon group which is in straight or branched chain form and optionally contains a cyclic structure, an aromatic ring group and a composite group thereof;

a part or all of the hydrogen atoms of $R^2$ are optionally substituted with a fluorine atom or a hydroxy group; $R^3$ is a hydrogen atom, a hydrocarbon group, a fluorine-containing alkyl group which is in straight or branched chain form and optionally contains a cyclic structure, or an aromatic ring group; the hydrocarbon group or fluorine-containing alkyl group of $R^3$ optionally contains a divalent linking group selected form an ether group (—O—) and a carbonyl group (—(C═O)—); m is an integer selected from 1 and 2; and, when m is 2, two $R^3$ are the same or different,

[Phenolic Compound A]

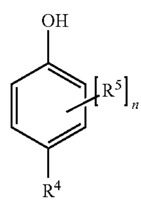

(2)

where $R^4$ and $R^5$ are each independently a hydrogen atom, a hydroxy group, an alkoxy group of 1 to 4 carbon atoms which is in straight or branched chain form, an alkyl group of 1 to 4 carbon atoms which is in straight or branched chain form, an alkyl group having a cyclic structure, or an unsubstituted aromatic ring group; $R^4$ and $R^5$ are the same or different; n is an integer selected from 1 and 2; and, when n is 2, a plurality of $R^5$ are the same or different,

[Phenolic Compound B]

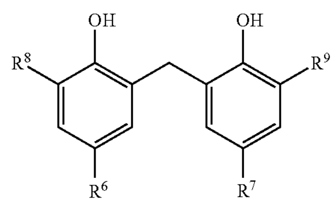

(3)

where $R^6$, $R^7$, $R^8$ and $R^9$ are each independently a hydrogen atom, a hydroxy group, an alkoxy group of 1 to 4 carbon atoms which is in straight or branched chain form, an alkyl group of 1 to 4 carbon atoms which is in straight or branched chain form, an alkyl group having a cyclic structure, or an aromatic ring group; and $R^6$, $R^7$, $R^8$ and $R^9$ are the same or different.

2. The purification method according to claim 1, wherein $R^4$ and $R^5$ in the phenolic compound A are each independently selected from the group consisting of a hydrogen atom, a methyl group, a methoxy group, an ethyl group, an ethoxy group, a n-propyl group, a n-propyloxy group, an i-propyl group, an i-propyloxy group, a n-butyl group, a n-butyloxy group, an i-butyl group, an i-butyloxy group, a t-butyl group, a t-butyloxy group and a hydroxy group with the proviso that at least one of $R^4$ and $R^5$ is not a hydrogen atom, and wherein $R^6$, $R^7$, $R^8$ and $R^9$ in the phenolic compound B are each independently selected from the group consisting of a hydrogen atom, a methyl group, a methoxy group, an ethyl group, an ethoxy group, a n-propyl group, a n-propyloxy group, an i-propyl group, an i-propyloxy group, a n-butyl group, a n-butyloxy group, an i-butyl group, an i-butyloxy group, a t-butyl group, a t-butyloxy group and a hydroxy group with the proviso that at least one of $R^6$, $R^7$, $R^8$ and $R^9$ is not a hydrogen atom.

3. The purification method according to claim 1, wherein the phenolic compound A is at least one compound selected from the group consisting of 6-tert-butyl-2,4-xylenol and methoquinone, and wherein the phenolic compound B is at least one compound selected from the group consisting of 2,2'-methylene-bis(4-methyl-6-tert-butylphenol) and 2,2'-methylene-bis(4-ethyl-6-tert-butylphenol).

4. The purification method according to claim 1, wherein the phenolic compound A is 6-tert-butyl-2,4-xylenol; and wherein the phenolic compound B is 2,2'-methylene-bis (4-methyl-6-tert-butylphenol).

5. The purification method according to claim 1, wherein a mass ratio of the phenolic compound A and the phenolic compound B is in a range of 1:0.1 to 1:10.

6. The purification method according to claim 1, wherein the fluorine-containing polymerizable monomer of the formula (1) is a fluorine-containing polymerizable monomer of the following formula (1a), (1b) or (1c)

(1a)

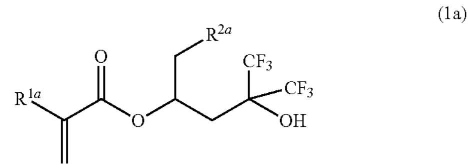

(1b)

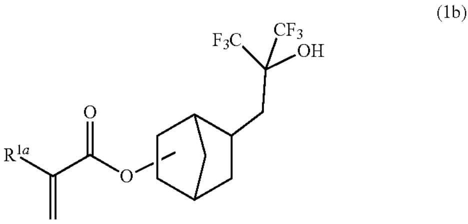

(1c)

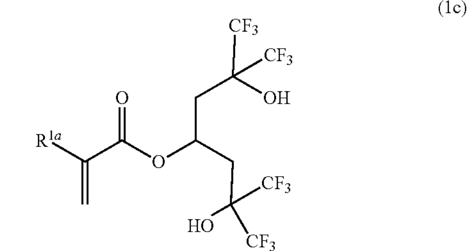

where $R^{1a}$ is a hydrogen atom, a methyl group, an ethyl group, a n-propyl group, an isopropyl group, a n-butyl group, a sec-butyl group, a tert-butyl group, a fluoromethyl group, a difluoromethyl group, a trifluoromethyl group, or a perfluoroethyl group; and $R^{2a}$ is a hydrogen atom, a methyl group, an ethyl group, a n-propyl group, an isopropyl group, a n-butyl group, a sec-butyl group, a tert-butyl group, a fluoromethyl group, a difluoromethyl group, a trifluoromethyl group, or a perfluoroethyl group.

7. The purification method according to claim 1, wherein the fluorine-containing polymerizable monomer of the formula (1) is a product of condensation between a compound of the following formula (5) and a compound of the following formula (6), and wherein the condensation is performed in the presence of at least one of the phenolic compound A and the phenolic compound B (5)

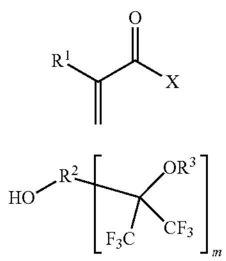

where X is a hydroxy group, a halogen atom, an alkoxy group, or an oxocarbonyl group; and the definitions of symbols other than X are the same as in the formula (1).

8. A method of producing a fluorine-containing polymer with a repeating unit of the following general formula (4), comprising:

a first step of obtaining a fluorine-containing polymerizable monomer of the following formula (1) by the purification method according to claim 1; and a second step of polymerizing the fluorine-containing polymerizable monomer obtained by the first step, thereby forming the fluorine-containing polymer with the repeating unit of the general formula (4)

(1)

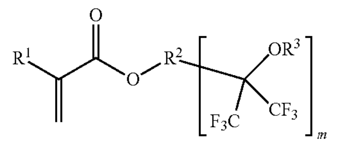

where $R^1$ is a group selected from a hydrogen atom, a halogen atom, a hydrocarbon group and a fluorine-containing alkyl group which is in straight or branched chain form and optionally contains a cyclic structure; $R^2$ is a divalent or trivalent organic group selected from an aliphatic hydrocarbon group which is in straight or branched chain form and optionally contains a cyclic structure, an aromatic ring group and a composite group thereof;

a part or all of hydrogen atoms of $R^2$ are optionally substituted with a fluorine atom or hydroxy group; $R^3$ is a hydrogen atom, a hydrocarbon group, a fluorine-containing alkyl group which is in straight or branched chain form and optionally contains a cyclic structure, or an aromatic ring group; the hydrocarbon group or fluorine-containing alkyl group of $R^3$ optionally contains a divalent linking group selected from an ether group (—O—) and a carbonyl group (—(C═O)—);

m is an integer selected from 1 to and 2; and, when m is 2, two $R^3$ are the same or different;

(4)

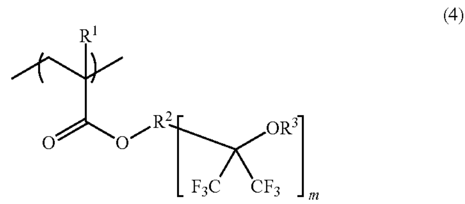

wherein the definitions of $R^1$, $R^2$, $R^3$ and m are the same as in the general formula (1).

* * * * *